(12) United States Patent
Lehmann et al.

(10) Patent No.: US 6,548,534 B2
(45) Date of Patent: Apr. 15, 2003

(54) NONSTEROIDAL GESTAGENS

(75) Inventors: Manfred Lehmann, Berlin (DE); Klaus Schoellkopf, Berlin (DE); Peter Strehlke, Berlin (DE); Nikolaus Heinrich, Berlin (DE); Karl-Heinrich Fritzemeier, Berlin (DE); Rolf Krattenmacher, Berlin (DE); Hans-Peter Muhn, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/915,453

(22) Filed: Jul. 27, 2001

(65) Prior Publication Data

US 2002/0016365 A1 Feb. 7, 2002

Related U.S. Application Data

(62) Division of application No. 09/662,143, filed on Sep. 14, 2000, now Pat. No. 6,344,454, which is a division of application No. 09/086,590, filed on May 29, 1998, now Pat. No. 6,245,804.
(60) Provisional application No. 60/082,789, filed on Apr. 23, 1998.

(30) Foreign Application Priority Data

May 30, 1997 (DE) .......................... 197 23 722

(51) Int. Cl.⁷ .................. A61K 31/136; A61K 31/167; A61K 31/195; C07C 235/26
(52) U.S. Cl. .............. 514/435; 514/510; 514/622; 514/625; 514/646; 514/653; 549/75; 549/76; 549/77; 560/43; 564/170; 564/202; 564/355; 564/443
(58) Field of Search .............. 549/75, 76, 77; 560/43; 564/170, 202, 355, 443; 514/435, 510, 622, 625, 646, 653

(56) References Cited

FOREIGN PATENT DOCUMENTS

| EP | 002 892 | 7/1979 |
|----|---------|--------|
| EP | 040 932 | 12/1981 |
| EP | 173 516 | 3/1986 |
| EP | 253 500 | 1/1988 |
| EP | 253 503 | 1/1998 |

Primary Examiner—Richard L. Raymond
(74) Attorney, Agent, or Firm—Millen, White, Zelano&Branigan, P.C.

(57) ABSTRACT

This invention describes the new, nonsteroidal gestagens of general formula I

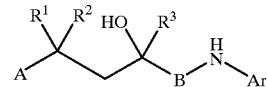

in which A, B, Ar¹, R¹, R² and R³ have the meanings that are indicated in more detail in the description. The new compounds show a very great affinity to the gestagen receptor. They can be used alone or in combination with estrogens in contraceptive preparations. In addition, they can be used for treating endometriosis. Together with estrogens, they can also be used in preparations for treating gynecological disorders, for treating premenstrual symptoms and for substitution therapy. Based on the androgenic action, they can also be used for male birth control, male HRT and hormone therapy and for treating andrological disease agents.

25 Claims, No Drawings

NONSTEROIDAL GESTAGENS

This application claims the benefit of the filiing date of U.S. provisional application Ser. No. 60/082,789, filed Apr. 23, 1998.

This application is a divisional of Ser. No. 09/662,143, filed Sep. 14, 2000, now U.S. Pat. No. 6,344,434, which is a division of Ser. No. 09/086,590, filed May 29, 1998 now U.S. Pat. No. 6,245,804.

This invention relates to nonsteroidal compounds, which have a high gestagenic activity.

In addition to a large number of steroid compounds with gestagenic action, gestagens that are not steroids are also known (for example from EP 0 253 500 B1 and WO 94/01412, cf. J. Med. Chem. 38 (1995) 4878).

This invention describes the compounds of general formula I $$\underset{A}{\overset{R^1\ R^2}{\diagdown}}\underset{B}{\overset{HO\ R^3}{\diagup}}\underset{Ar}{\overset{H}{N}}$$

I in which $R^1$ and $R^2$ are the same or different and stand for a hydrogen atom, a $C_1$–$C_5$ alkyl group or a halogen atom, and also together with the C-atom of the chain stand for a ring with a total of 3–7 links, $R^3$ stands for a $C_1$–$C_5$ alkyl group or a partially or completely fluorinated $C_1$–$C_5$ alkyl group, A stands for a monocyclic or bicyclic aromatic ring that is optionally substituted by one or more radicals, selected from halogen atoms, $C_1$–$C_5$ alkyl groups, $C_2$–$C_5$ alkenyl groups —$CR^5$=$CR^6R^7$, whereby $R^5$, $R^6$ and $R^7$ are the same or different and, independently of one another, mean hydrogen atoms or $C_1$–$C_5$ alkyl groups; hydroxy groups, hydroxy groups that carry a $C_1$–$C_{10}$ acyl group, a $C_3$–$C_{10}$ carbalkoxyalkyl group, a $C_2$–$C_5$ cyanalkyl group, a $C_3$–$C_{10}$ unsubstituted or substituted allyl group, a $C_3$–$C_{10}$ unsubstituted or substituted propargyl group, a $C_2$–$C_5$ alkoxyalkyl group, a $C_1$–$C_5$ alkyl group that is partially or completely substituted by fluorine atoms, the cyano or nitro group, $C_1$–$C_5$ alkoxy groups, $C_1$–$C_5$ alkylthio groups, mono- or disubstituted $C_1$–$C_{10}$ amino groups or partially or completely fluorinated $C_1$–$C_5$ alkyl groups, for an ester group —$COOR^4$, whereby $R^4$ means a $C_1$–$C_5$ alkyl group, for a $C_2$–$C_5$ alkenyl group —$CR^5$=$CR^6R^7$, whereby $R^5$, $R^6$ and $R^7$ are the same or different, and, independently of one another, mean hydrogen atoms, halogen atoms, aryl radicals or $C_1$–$C_5$ alkyl groups, for an alkinyl group —C=$CR^5$, whereby $R^5$ means a hydrogen atom or a $C_1$–$C_5$ alkyl group, for a partially or completely fluorinated $C_1$–$C_5$ alkyl group, B stands for a carbonyl group or a $CH_2$ group, and Ar stands for a ring system, selected from the group of general partial formulas 2–11, -continued

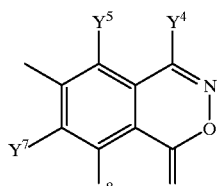

10

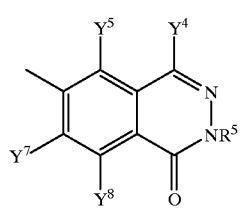

11 in which
radicals $X^{3a}$, $X^4$, $X^6$, $X^7$ (in partial formula 2), $X^4$, $X^6$, $X^7$ (in partial formulas 3 and 4), $X^{3a}$, $X^{3b}$, $X^4$, $X^6$, $X^7$ (in partial formulas 5, 6 and 7) or $Y^4$, $Y^5$, $Y^7$, $Y^8$ (in partial formulas 8, 9, 10 and 11) are the same or different and are selected from hydrogen atoms, $C_1$–$C_5$ alkyl groups, which in addition can contain a hydroxy group that is optionally etherified with a $C_1$–$C_5$ alkyl group or esterified with a $C_1$–$C_5$ alkanoyl group, partially or completely fluorinated $C_1$–$C_5$ alkyl groups, $C_2$–$C_5$ alkenyl groups —$CR^5$=$CR^6R^7$, whereby $R^5$, $R^6$, and $R^7$ have the above-mentioned meaning, alkinyl groups —C≡$CR^5$, whereby $R^5$ has the above-mentioned meaning,
radicals $X^{3a}$ and $X^{3b}$ also together with the C-atom of benzocondensed ring system 5, 6 or 7 can form a ring with a total of 3–7 links,
and moreover, radicals $X^4$, $X^6$, $X^7$ (in partial formulas 2, 3, 4, 5, 6 and 7) or $Y^4$, $Y^5$, $Y^7$, $Y^8$ (in partial formulas 8, 9, 10 and 11) are selected from halogen atoms, hydroxy groups, $C_1$–$C_5$ alkoxy groups or $C_1$–$C_5$ alkanoyloxy groups, also if B in general formula I stands for a $CH_2$ group, Ar in addition stands for a phenyl radical of general partial formula 12,

12

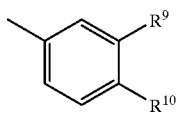

in which $R^9$ and $R^{10}$ are the same or different and mean a cyano group, a nitro group, a halogen atom, a $C_1$–$C_5$ alkyl group, a $C_1$–$C_5$ alkoxy group, a partially or completely fluorinated $C_1$–$C_5$ alkyl group, a $C_1$–$C_5$ alkylthio group, a $C_1$–$C_5$ alkylsulfinyl group or a $C_1$–$C_5$ alkylsulfonyl group, and if B stands for a $CH_2$ group, the physiologically compatible salts of the compounds of general formula I with acids.

The compounds according to the invention are distinguished from the known nonsteroidal compounds with gestagenic action by the substitution pattern on the aryl radical that is on the right in general formula I. In the compounds that are present here, Ar is a benzocondensed, bicyclic ring system, while in the structures that are known from EP 0 253 500 B1 and that can be considered as the closest compounds, a phenyl radical that is substituted in one, two or three places is at this point.

The compounds of general formula I according to the invention can be present as different stereoisomers because of the presence of asymmetry centers. Both the racemates and the stereoisomers that are detached are part of the subject of this invention.

The substituents that are defined as groups in the compounds of general formula I can have the following meanings in each case.

$C_1$–$C_5$ Alkyl groups can readily be a methyl, ethyl, n-propyl, isopropyl, n-, iso-, tert-butyl group or an n-pentyl, 2,2-dimethylpropyl or 3-methylbutyl group. A methyl or ethyl group is preferred.

A fluorine, chlorine, bromine or iodine atom can stand for a halogen atom. Here, fluorine, chlorine or bromine is preferred.

If $R^1$ and $R^2$ together with the C-atom of the chain form a 3–7-membered ring, this is, for example, a cyclopropyl, cyclobutyl, cyclopentyl or cyclohexyl ring. The cyclopropyl ring is preferred.

For a partially or completely fluorinated $C_1$–$C_5$ alkyl group, the perfluorinated alkyl groups that appear above and of the latter mainly the trifluoromethyl group or pentafluoroethyl group as well as partially fluorinated alkyl groups, for example, the 5,5,5,4,4-pentafluoropentyl group or 5,5,5, 4,4,3,3-heptafluoropentyl group are considered.

As a $C_2$–$C_5$ alkenyl group, for example, a vinyl-, allyl- or 2,3-dimethyl-2-propenyl group can appear; if aromatic compound A is substituted with an alkenyl group, preferably it is a vinyl group.

Representatives of a $C_1$–$C_5$ alkoxy group are selected from methoxy, ethoxy, n-propoxy, iso-propoxy, n-, iso-, tert-butoxy groups or n-pentoxy, 2,2-dimethylpropoxy or 3-methylbutoxy groups. A methoxy or ethoxy group is preferred.

$C_1$–$C_5$ Perfluoroalkoxy groups are the corresponding perfluorinated radicals of the $C_1$–$C_5$ alkoxy groups above.

Monocyclic or bicyclic aromatic ring A, which can be substituted, is a carbocyclic or heterocyclic aryl radical.

In the first case, this is, for example, a phenyl or naphthyl radical, preferably a phenyl radical.

As a heterocyclic radical, for example, a monocyclic heterocyclic radical can be, for example, the thienyl, furyl, pyranyl, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl, tetrazolyl radical, specifically all possible isomers relative to the positions of the heteroatoms. The thienyl radical is preferred as heteroaryl radical A.

For $R^4$, a methyl, ethyl, n- or iso-propyl group is preferred as a $C_1$–$C_5$ alkyl group in ester group —$COOR^4$.

As a $C_1$–$C_5$ alkyl group for etherification of hydroxy groups, the above-mentioned alkyl groups are suitable, primarily a methyl or ethyl group.

As a $C_1$–$C_5$ alkanoyl group for esterification of hydroxy groups, a formyl, acetyl, propionyl, butyryl, isobutyl, valeryl or isovaleryl group is suitable, preferably an acetyl group.

If $X^{3a}$ and $X^{3b}$ together with the C-atom of the benzocondensed ring system form a 3–7-membered ring, this is, for example, a cyclopropyl, cyclobutyl, cyclopentyl or cyclohexyl ring. The cyclopropyl ring is preferred.

As a $C_1$–$C_5$ alkanoyloxy group for $X^4$, $X^6$, $X^7$, $Y^4$, $Y^5$, $Y^7$ or $Y^8$, a formyloxy, acetoxy, propinoyloxy, butyryloxy, iso-butyryloxy, valeryloxy or isovaleryloxy group is suitable, preferably an acetoxy group.

The above-mentioned $C_1$–$C_5$ alkyl groups can stand for $C_1$–$C_5$ alkyl within the $C_1$–$C_5$ alkylthio, $C_1$–$C_5$ alkylsulfinyl or $C_1$–$C_5$ alkylsulfonyl group.

If the compounds of general formula I (B=—CH$_2$) are present as salts, this can be in the form of, for example, hydrochloride, sulfate, nitrate, tartrate or benzoate.

If the compounds according to the invention are present as racemic mixtures, they can be separated into pure, optically active forms according to the methods of racemate separation that are familiar to one skilled in the art. For example, the racemic mixtures can be separated by chromatography into pure isomers on an even optically active carrier material (CHIRALPAK AD$^{(R)}$). It is also possible to esterify the free hydroxy group in a racemic compound of general formula I with an optically active acid and to separate the diastereoisomeric esters that are obtained by fractionated crystallization or by chromatography, and to saponify the separate esters in each case into the optically pure isomers. For example, mandelic acid, camphorsulfonic acid or tartaric acid can be used as optically active acid.

Preferred according to this invention are those compounds of general formula I, in which:

R$^1$ and R$^2$ are the same or different and stand for a hydrogen atom, a methyl or ethyl group, and also together with the C-atom of the chain stand for a cyclopropyl ring, and/or R$^3$ stands for a C$_1$–C$_5$ perfluoroalkyl group, and/or A stands for a benzene, naphthalene or thiophene ring that is optionally substituted by one or more radicals, selected from fluorine atoms, chlorine atoms, bromine atoms, methyl groups, ethyl groups, (CH$_2$)$_n$ group (n=3,4,5), which with 2 adjacent C atoms of aromatic compound A forms a ring with n+2 links and can contain unsaturations; vinyl groups, hydroxy groups, methoxy groups, ethoxy groups, and/or either X$^{3a}$ stands for a hydrogen atom or a C$_1$–C$_5$ alkyl group, or X$^{3a}$ and X$^{3b}$ are the same or different and stand for a hydrogen atom or a C$_1$–C$_5$ alkyl group and/or X$^4$, X$^6$ and X$^7$ are the same or different, and stand for, independently of one another, a hydrogen atom or a halogen atom, and/or Y$^4$ stands for a C$_1$–C$_5$ alkyl group or a C$_1$–C$_5$ perfluoroalkyl group, and/or Y$^5$, Y$^7$ and Y$^8$ are the same or different and, independently of one another, stand for a hydrogen atom or a halogen atom, and the other substituents all have the meanings that are indicated in Formula 1.

In addition, those compounds of general formula I in which Ar stands for a ring system of partial formula 6, 7, 10 or 11 are preferred.

The compounds that are mentioned below are especially preferred according to the invention:

4-Bromo-5-(2-hydroxy-4-methyl-4-phenyl-2-trifluoromethyl-valeroylamino)-phthalide, 6-bromo-5-(2-hydroxy-4-methyl-4-phenyl-2-trifluoromethyl-valeroylamino)-phthalide, 5-(2-hydroxy-4-methyl-2-pentafluoroethyl-4-phenyl-valeroylamino)-phthalide, 5-[2-hydroxy-4-(3-methoxyphenyl)-4-methyl-2-trifluoromethyl-valeroylamino]-phthalide, 5-[2-(hydroxy-4-(4-methoxyphenyl)-4-methyl-2-trifluoromethyl-valeroylamino]-phthalide, 5-[2-hydroxy-4-(2-hydroxyphenyl)-4-methyl-2-trifluoromethyl-valeroylamino]-phthalide, 5-[4-(2-fluorophenyl)-2-hydroxy-4-methyl-2-trifluoromethyl-valeroylamino]-phthalide, 5-[4-(4-fluorophenyl)-2-hydroxy-4-methyl-2-trifluoromethyl-valeroylamino]-phthalide, 5-[4-(4-chlorophenyl)-2-hydroxy-4-methyl-2-trifluoromethyl-valeroylamino]-phthalide, 5-[4-(4-bromophenyl)-2-hydroxy-4-methyl-2-trifluoromethyl-valeroylamino]-phthalide, 5-[2-hydroxy-4-methyl-4-(4-tolyl)-2-trifluoromethyl-valeroylamino]-phthalide, 5-[2-hydroxy-4-methyl-4-(3-tolyl)-2-trifluoromethyl-valeroylamino]-phthalide, 5-[4-(4-cyanophenyl)-2-hydroxy-4-methyl-2-trifluoromethyl-valeroylamino]-phthalide, 5-[4-(3,4-dimethylphenyl)-2-hydroxy-4-methyl-2-trifluoromethyl-valeroylamino]-phthalide, 5-[4-(3,5-dimethylphenyl)-2-hydroxy-4-methyl-2-trifluoromethyl-valeroylamino]-phthalide, 5-[2-hydroxy-4-(2-methoxy-5-methylphenyl)-4-methyl-2-trifluoromethyl-valeroylamino]-phthalide, 5-[4-(5-chloro-2-hydroxyphenyl)-2-hydroxy-4-methyl-2-trifluoromethyl-valeroylamino]-phthalide, 5-[4-(5-fluoro-2-hydroxyphenyl)-2-hydroxy-4-methyl-2-trifluoromethyl-valeroylamino]-phthalide, 5-[2-hydroxy-4-(2-hydroxy-5-methylphenyl)-4-methyl-2-trifluoromethyl-valeroylamino]-phthalide, 5-[4-(5-fluoro-2-methoxyphenyl)-2-hydroxy-4-methyl-2-trifluoromethyl-valeroylamino]-phthalide, 5-[4-(2-fluoro-4-methoxyphenyl)-2-hydroxy-4-methyl-2-trifluoromethyl-valeroylamino]-phthalide, 5-[4-(3-fluoro-4-methoxyphenyl)-2-hydroxy-4-methyl-2-trifluoromethyl-valeroylamino]-phthalide, 5-(2-hydroxy-4-phenyl-2-trifluoromethyl-valeroylamino)-phthalide, 5-[2-hydroxy-4-(2-methoxyphenyl)-4-methyl-2-trifluoromethyl-valeroylamino]-phthalide, 5-[4-(5-chloro-2-methoxyphenyl)-2-hydroxy-4-methyl-2-trifluoromethyl-valeroylamino]-phthalide, 5-(2-hydroxy-4-phenyl-2-trifluoromethyl-pentylamino)-phthalide, 5-(2-hydroxy-4-methyl-4-phenyl-2-trifluoromethyl-pentylamino)-phthalide, 5-[4-(4-fluorophenyl)-2-hydroxy-4-methyl-2-trifluoromethyl-pentylamino]-phthalide, 5-[4-(5-fluoro-2-hydroxyphenyl)-2-hydroxy-4-methyl-2-trifluoromethyl-pentylamino]-phthalide, 6-acetyl-5-(2-hydroxy-4-methyl-4-phenyl-2-trifluoromethyl-valeroylamino)-phthalide, 5-[4-(3-fluoro-4-hydroxyphenyl)-2-hydroxy-4-methyl-2-trifluoromethyl-valeroylamino]-phthalide, 5-[4-(3-fluorophenyl)-2-hydroxy-4-methyl-2-trifluoromethyl-valeroylamino]-phthalide, 6-(3-hydroxy-3-methyl-1-butinyl)-5-(2-hydroxy-4-methyl-4-phenyl-2-trifluoromethyl-valeroylamino)-phthalide, 6-[2-hydroxy-4-methyl-4-phenyl-2-trifluoromethyl-valeroylamino)-4-methyl-2,3-benzoxazin-1-one, 6-(2-hydroxy-4-methyl-4-phenyl-2-trifluoromethyl-valeroylamino)-4-trifluoromethyl-2,3-benzoxazin-1-one, 4-ethyl-6-(2-hydroxy-4-phenyl-2-trifluoromethyl-pentylamino)-2,3-benzoxazin-1-one, 4-ethyl-6-[2-hydroxy-4-(2-methoxyphenyl)-4-methyl-2-trifluoromethyl-valeroylamino]-2,3-benzoxazin-1-one, 6-[2-hydroxy-4-(2-methoxyphenyl)-4-methyl-2-trifluoromethyl-valeroylamino]-4-methyl-2,3-benzoxazin-1-one, 4-ethyl-6-[2-hydroxy-4-methyl-4-(4-methylphenyl)-2-trifluoromethyl-valeroylamino]-2,3-benzoxazin-1-one, 6-[4-(4-bromophenyl)-2-hydroxy-4-methyl-2-trifluoromethyl-valeroylamino]-4-ethyl-2,3-benzoxazin-1-one, 4-ethyl-6-[4-(5-fluoro-2-methoxyphenyl)-2-hydroxy-4-methyl-2-trifluoromethyl-valeroylamino]-2,3-benzoxazin-1-one, 6-[4-(5-fluoro-2-methoxyphenyl)-2-hydroxy-4-methyl-2-trifluoromethyl-valeroylamino]-4-methyl-2,3-benzoxazin-1-one,
1-(4-nitro-3-trifluoromethylanilino)-4-phenyl-2-trifluoromethyl-2-pentanol,
1-(4-nitro-3-trifluoromethylanilino)-4-phenyl-2-trifluoromethyl-2-pentanol,
5-(2-hydroxy-4,4-dimethyl-2-trifluoromethyl-5-hexenoylamino)-phthalide,
5-[2-hydroxy-3-(1-phenyl-cyclopropyl)-2-trifluoromethyl-propionylamino]-phthalide,
5-[2-hydroxy-3-(1-phenyl-cyclobutyl)-2-trifluoromethyl-propionylamino]-phthalide,
5-[2-hydroxy-3-(1-phenyl-cyclohexyl)-2-trifluoromethyl-propionylamino]-phthalide,
2-hydroxy-4-methyl-2-trifluoromethyl-4-(4-vinylphenyl)-valeric acid,
4-(4-acetylphenyl)-2-hydroxy-4-methyl-2-trifluoromethyl-valeric acid,
4-(4-acetyl-3-methoxyphenyl)-2-hydroxy-4-methyl-2-trifluoromethyl-valeric acid,
4-(4-cyanophenyl)-2-hydroxy-4-methyl-2-trifluoromethyl-valeric acid,
4-(4-carbamoylphenyl)-2-hydroxy-4-methyl-2-trifluoromethyl-valeric acid,
4-(4-cyano-2-methoxyphenyl)-2-hydroxy-4-methyl-2-trifluoromethyl-valeric acid,
4-(3-bromo-4-methoxyphenyl)-2-hydroxy-4-methyl-2-trifluoromethyl-valeric acid,
2-Hydroxy-4-methyl-4-(3-nitro-4-methoxyphenyl)-2-trifluoromethyl-valeric acid,
4-(4-iodo-2-methoxyphenyl)-4-methyl-2-oxo-valeric acid,
4-(3-chlorophenyl)-4-methyl-2-oxo-valeric acid,
4-(3-bromophenyl)-4-methyl-2-oxo-valeric acid,
4-(2-iodophenyl)-4-methyl-2-oxo-valeric acid,
4-(3-iodophenyl)-4-methyl-2-oxo-valeric acid,
4-(4-iodophenyl)-4-methyl-2-oxo-valeric acid,
4-(5-fluoro-2-methoxyphenyl)-4-methyl-2-oxo-valeric acid,
4-(4-bromo-2-methoxyphenyl)-2-oxo-valeric acid,
3-(1-phenylcyclopentyl)-pyruvic acid,
6-[3-(1-phenyl-cyclopropyl)-2-oxo-propionylamino]-4-methyl-2,3-benzoxazin-1-one,
6-[3-(1-phenyl-cyclobutyl)-2-oxo-propionylamino]-4-methyl-2,3-benzoxazin-1-one,
6-[3-(1-phenyl-cyclohexyl)-2-oxo-propionylamino]-4-methyl-2,3-benzoxazin-1-one,
5-[4-(4-iodo-2-methoxyhenyl)-4-methyl-2-oxo-valeroylamino)-phthalide,
5-[4-(4-iodophenyl)-4-methyl-2-oxo-valeroylamino)-phthalide,
5-[4-(3-iodophenyl)-4-methyl-2-oxo-valeroylamino)-phthalide,
5-[4-(4-bromo-2-methoxyhenyl)-2-oxo-valeroylamino)-phthalide,
5-[3-(1-phenyl-cyclopentyl)-2-oxo-propionylamino]-phthalide,
6-[4-(5-fluoro-2-methoxyhenyl)-4-methyl-2-oxo-valeroylamino)-4-methyl-2,3-benzoxazin-1-one,
6-[4-(5-fluoro-2-methoxyphenyl)-4-methyl-2-oxo-valeroylamino)-4-ethyl-2,3-benzoxazin-1-one,
6-(2-hydroxy-2,4-dimethyl-4-phenyl-valeroylamino)-4-methyl-2,3-benzoxazin-1-one,
5-[4-(3-chloro-4-methoxyphenyl)-2-hydroxy-4-methyl-2-trifluoromethyl-valeroylamino)-phthalide,
5-[4-(3-chloro-4-hydroxyphenyl)-2-hydroxy-4-methyl-2-trifluoromethyl-valeroylamino]-phthalide.

All above-mentioned compounds are especially preferred in the form of the optical antipodes or the separate diastereomers.

In the gestagen receptor bonding test on the gestagenic action using cytosol from rabbit uterus homogenate and from $^3$H-progesterone as a reference substance, the new compounds show a strong to very strong affinity to the gestagen receptor (see Table 1).

TABLE 1

| Example No. | Structure | Competition Factor (Reference Substance $^1$H-Progesterone) |
| --- | --- | --- |
| (*) (Melting point 141–142° C.) | 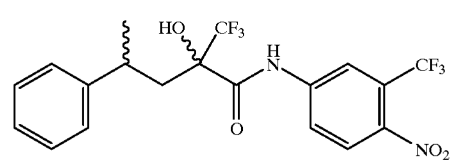 | 17 |
| (*) (Melting point 161° C.) | 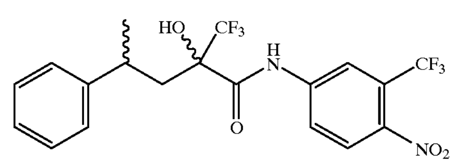 | 2.0 |
| 65 | 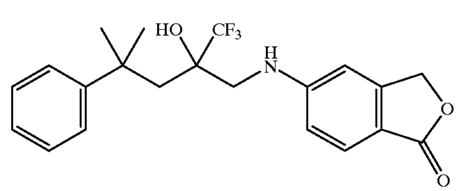 | 0.17 |

TABLE 1-continued

| Example No. | Structure | Competition Factor (Reference Substance $^1$H-Progesterone) |
|---|---|---|
| 104 | [structure: phenyl-CH(CH₃)-CH₂-C(CF₃)(OH)-C(=O)-NH- attached to methyl-substituted benzoxazinone] | 0.1 |
| 106 | [structure: phenyl-C(CH₃)₂-CH₂-C(CF₃)(OH)-C(=O)-NH- attached to methyl-substituted benzoxazinone] | 0.55 |

(*) EP 0 253 500 B1, Example 1

In addition to their gestagenic action, which is pronounced to different degrees depending on the compound of general formula I that is considered, the new compounds also are distinguished by a more or less strongly pronounced affin-ity to the androgen receptor. The androgen receptor bonding test on androgenic action was carried out using cytosol that consists of rat prostate homogenate and $^3$H-methyltrienolone as a reference substance.

The new compounds are thus represented relative to the gestagenic compounds from EP 0 253 500 B1 as compounds with a quite novel mix profile, which consists of gestagenic and androgenic action.

For the compounds of general formula I according to the invention, in this case all three of the cases that are pos-sible below are found, which based on the competition factors on progesterone receptor ($KF_{Prog}$) and androgen receptor ($KF_{Andro}$) are classified within the scope of this invention as follows:
1) Compounds with stronger gestagenic action and less pronounced androgenic action ($KF_{Prog}$<1 and $KF_{Andro}$>5);
2) Compounds with stronger androgenic action and less pronounced gestagenic action ($KF_{Andro}$<5 and $KF_{Prog}$>1);
3) Compounds with pronounced gestagenic and pronounced androgenic action ($KF_{Prog}$<1 and $KF_{Andro}$<5).

Depending on their classification according to 1), 2) or 3), the new compounds according to the invention can be used for different medical or pharmaceutical purposes.

In the case of the compounds that are classified under 1) with stronger gestagenic action and less pronounced androgenic action, these are very effective gestagens, which, like the already numerous known gestagenic compounds, are suitable for preserving pregnancies in the case of parenteral administration and in the case of oral administration.

In combination with an estrogen, combination preparations are obtained that can be used for contraception and for the treatment of menopausal symptoms.

Based on their high gestagenic action, the new compounds of general formula I that are classified under 1) can be used, for example, alone or in combination with estrogens in contraceptive preparations. However, all other applications that are known for gestagen are now open to these new compounds (see, e.g., "Kontrazeption mit Hormonen [Contraception with Hormones]," Hans-Dieter Taubert and Herbet Kuhl, Georg Thieme Verlag Stuttgart—New York, 1995).

Suitable dosages can be determined as a matter of routine, e.g., by determining the bioequivalency, for example in the pregnancy-maintenance test, relative to a known gestagen for a specific use, for example an amount that is bioequivalent to 30 to 150 µg of levonorgestrel for contraception.

The dosage of the compounds according to the invention under 1) in contraceptive preparations is preferably to be 0.01 to 2 mg per day.

The gestagenic and estrogenic active ingredient components are preferably administered orally together in contraceptive preparations. The daily dose is preferably administered once.

As estrogens, all natural and synthetic compounds that are known as estrogenically active are suitable.

As natural estrogens, these are especially estradiol and also its longer-acting esters, such as valerate, etc. or estriol.

Preferably, however, synthetic estrogens such as ethinyl-estradiol, 14α,17α-ethano-1,3,5(10)-estratriene-3–17β-diol (WO 88/01275), 14α,17α-ethano-1,3,5(10)-estratriene-3, 16α,17β-triol (WO 91/08219) or the 15,15-diallyl derivatives of the estradiol, and of these especially 15,16-dimethylestradiol (WO 95/04070) can be mentioned. As a synthetic estrogen, ethinylestradiol is preferred.

Also, the estratrien-3-aminosulfonates that have become known recently (WO 96/05216 and WO 96/05217), derived from estradiol or ethinylestradiol, which are distinguished by low hepatic estrogeneity, are suitable as estrogens for common use with the compounds of general formula I that are classified under 1). Finally, the 14α,15α-methylene steroids from the estrane series, especially the 14α,15α-methylene-17α-estradiol as well as the corresponding 3-aminosulfonate derivatives can be mentioned.

The estrogen is administered in an amount that corresponds to that of 0.01 to 0.05 mg of ethinylestradiol.

The new compounds of general formula I that are classified under 1) can also be used in preparations for treatment of gynecological disorders and for substitution therapy.

Because of their advantageous profile of action, these compounds according to the invention are especially well suited for treatment of premenstrual symptoms, such as headaches, depres-sion, water retention and mastodynia. The daily dose in the treatment of premenstrual symptoms is approximately 1 to 20 mg.

Analogously to what is already known for other gestagens, the new compounds can also be used for treating endometrioses.

Finally, these new compounds can also be used as gestagenic components in the compositions for female birth control that have recently become known and that are distinguished by the additional use of a competitive progesterone antagonist (H. B. Croxatto and A. M. Salvatierra in Female Contraception and Male Fertility Regulation, ed. by Runnebaum, Rabe & Kiesel—Vol. 2, Advances in Gynecological and Obstetric Research Series, Parthenon Publishing Group—1991, page 245; WO 93/17686, WO 93/21927, U.S. Pat. No. 5,521,166).

The dosage lies in the range that is already indicated, and the formulation can be carried out as in conventional OC-preparations. The administration of the additional, competitive progesterone antagonist can in this case also be performed sequentially.

Those compounds of the general formula, which are to be categorized as above under 2) and 3), i.e., compounds that have a strong androgenic action (androgenic gestagens), can be used for the production of pharmaceutical preparations for male birth control.

Currently, in several WHO studies, the contraceptive action of a combination that consists of an orally administered gestagen (Depot-medroxy progesterone acetate, levonorgestrel ester, cyproterone acetate) is tested on men with a parenterally administered androgen (testosterone oenanthate).

By contrast, birth control in men is possible with these compounds in one dosage form, specifically an oral dosage form or a dosage form that is to be administered transdermally.

In addition, the compounds according to the invention with androgenic action can be used with older males for male HRT (Hormone Replacement Therapy).

Those compounds of general formula I, which can more likely be classified under 2), i.e., compounds with mainly androgenic action and weaker gestagenic action, can be used for male hormone therapy. Preparations for treating a hypergonadism and for treating male infertility and disturbances of potency can be produced with them.

For male birth control and for treating the abovementioned androgenic disease agents, the compounds according to the invention are used in the dosages that are equivalent in action to the testosterone oenanthate amounts that are used in the WHO studies or to the dosage that is already in androgen therapy of compounds used.

Amounts that are equivalent in action are those amounts that, in the test on androgenic action on the seminal vesicles and/or prostate of the rat (Hershberger Test), achieve comparable action.

For HRT in man, to date a substitution dose of approximately 10 mg/day of testosterone oenanthate is used.

For male birth control studies that are performed by the WHO, different testosterone esters (oenanthate, bucyclate, undecanoate) are used in the range of approximately 10–30 mg/day.

At this point it should be pointed out that the transi-tions between 1), 2) and 3), as regards the correlation according to the invention of various indications with these varying mix profiles 1), 2) and 3), are smooth. The compounds that more likely lie on the edge of the indicated KF areas based on their $KF_{Prog}$ and/or $KF_{Andro}$, can easily be used also for the indications that are assigned to the adjacent mix profile.

The compounds of general formula I also partially show actions on the glucocorticoid and/or mineral corticoid receptor.

The formulation of the pharmaceutical preparations based on the new compounds is carried out in a way that is known in the art, by the active ingredient, optionally in combination with an estrogen, being processed with the vehicles that are commonly used in galenicals, diluents, optionally taste correctives, etc., and conveyed in the desired form of administration.

For the preferred oral administration, especially tablets, coated tablets, pills, suspension or solutions are suitable.

For parenteral administration, especially oily solutions, such as, for example, solutions in sesame oil, castor oil and cottonseed oil, are suitable. To increase solubility, solubilizers, such as, for example, benzyl benzoate or benzyl alcohol, can be added.

The compounds of general formula I can also be administered continuously by an intrauterine release system (intrauterine system=IUS; e.g., MIRENA$^{(R)}$); the release rate of the active compound(s), is selected in this case in such a way that the dose that is released daily lies within the already indicated dosage range. It is also possible to incorporate the substances according to the invention in a transdermal system and thus to administer them transdermally.

The compounds of general formula I according to the invention can be produced as described below.

Production Process

1. A carbonyl compound of general formula II

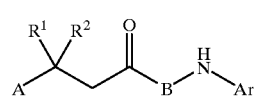

II in which A, B, Ar, $R^1$ and $R^2$ have the meaning that is indicated in formula I, is reacted with a compound of general formula $C_nF_{2n+1}$—$SiR^3$, in which $R^3$ has the meaning that is indicated in general formula 1, in the presence of a catalyst or with an alkyl metal compound, for example a Grignard reagent or a lithium alkyl, to a compound of formula I. As catalysts, fluoride salts or basic compounds such as alkali carbonates are suitable (J. Amer. Chem. Soc. 111, 393 (1989)).

2. A compound of general formula III

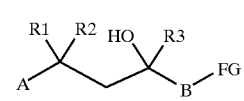

III in which A, B, $R^1$, $R^2$ and $R^3$ have the meaning that is indicated in formula 1 and FG means a leaving group, is reacted with a compound Ar—NH—$R^{11}$, whereby $R^{11}$ means a hydrogen atom or a $C_1$–$C_5$ acyl group, and Ar has the meaning that is indicated in general formula I, whereby optionally then radical $R^{11}$ is cleaved off to obtain a compound of formula I. In this case, the compound of general formula III optionally can be formed only as an intermediate product, e.g., this can be an acid chloride that is formed as an intermediate product from a corresponding carboxylic acid.

As leaving groups

3. A compound of general formula IV

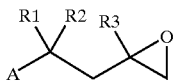

in which A, $R^1$, $R^2$ and $R^3$ have the meaning that is indicated in formula I, is reacted with a compound of formula Ar—NH—$R^{11}$, whereby $R^{11}$ and Ar have the above-indicated meanings, whereby optionally then radical $R^{11}$ is cleaved off, to obtain a compound of formula I with B in the meaning of a $CH_2$ group.

4. A compound of formula I, which in radical A or in radical Ar contains the grouping aryl-X, whereby "aryl" means an isocyclic or heterocyclic aromatic compound that corresponds to the definitions that are given for formula I and X means a bromine or iodine atom or the group —O—$SO_2R^{12}$, in which $R^{12}$ means a $C_1$–$C_5$ perfluoroalkyl group, is reacted under metal catalysis to compound aryl-$R^{13}$ according to processes that are known in the art with a compound of formula $R^{13}$-Y, whereby $R^{13}$ represents an optionally substituted aryl, ethenyl or ethinyl radical and Y represents a hydrogen atom (J. Org. Chem. 43, 2947 (1978)), group B (O—$R^{14}$)$_2$ (J. Org. Chem. 58, 2201 (1993)) or Sn($R^{15}$)$_3$ (J. Org. Chem. 52, 422 (1987)) with $R^{14}$ and $R^{15}$ meaning a phenyl radical or $C_1$–$C_5$ alkyl and $R^{14}$ also represents hydrogen, Mg-halogen or an alkali metal atom.

5. In a compound of formula I, which contains an alkoxy or acyloxy substituent in A or Ar, the OH group is released, and optionally etherified or esterified in another reaction or, after conversion into a 1-phenyl-5-tetrazolylether, is completely eliminated by hydrogenation (J. Amer. Chem. Soc. 88, 4271 (1966)).

Of all the foregoing process variants, 1. and 2. are suitable for the production of all compounds that fall under general formula I.

Compounds of general formula I can be produced with the third variant, in which B stands for a —$CH_2$ group.

Using the fourth and fifth process variants, functionalizations of already existing compounds of general formula I can be undertaken.

Compounds that were produced according to one of the processes above and in which A is an optionally substituted aromatic ring, optionally can be selectively substituted at this aromatic radical according to known processes. Examples of this process are the catalytic hydrogenation of multiple bonds, nitration and halogenation.

The starting materials that are used in the examples are produced as follows:

Production of Starting Materials

4-Methyl-4-phenyl-2-oxovaleric acid

A Grignard solution that is produced from 26.4 g of magnesium and 162 ml of 2-methyl-2-phenyl-1-chloropropane in 150 ml of diethyl ether was added in drops to 600 ml of oxalic acid diethyl ester at –30° C. After 2 hours at room temperature, it was added to ammonium chloride solution, extracted with diethyl ether, dried ($Na_2SO_4$) and distilled in fractionated form; 84 g of ethyl ester (boiling point 115–120° C./0.03 hPa), which is dissolved in 1 l of methanol, is obtained, mixed with 500 ml of 1 m sodium hydroxide and stirred for 1.5 hours at room temperature. After the methanol is evaporated in a vacuum, the residue is dispersed between water and diethyl ether, the aqueous phase is acidified with hydrochloric acid and extracted with diethyl ether. After concentration by evaporation, 57 g of 4-methyl-4-phenyl-2-oxovaleric acid is obtained as a thick oil.

4,4-Dimethyl-2-oxo-5-hexenoic acid 36 g of 3,3-dimethyl-4-pentenoic acid is obtained as an oil from 50 g of 3,3-dimethyl-4-pentenoic acid methyl ester by saponification with 10% potassium hydroxide. By stirring with thionyl chloride (20 hours, room temperature), the acid chloride is obtained, boiling point 59° C./30 hPa. 16 g of it is stirred with 15 g of trimethylsilylcyanide and 0.16 g of zinc iodide for 4 days. After distillation, 13 g of 4,4-dimethyl-2-oxo-5-hexenoic acid nitrile, boiling point 75–85° C./30 hPa, is obtained. 2 g of it is saturated with 0.6 ml of methanol in 13 ml of hexane while being cooled with ice with hydrochloric-acid gas, and it is mixed for 2 hours with water. From the hexane phase, after drying ($Na_2SO_4$) and concentration by evaporation, 0.558 g of 4,4-dimethyl-2-oxo-5-hexenoic acid methyl ester, boiling point 48° C./0.003 hPa, is obtained. 0.535 g of it is saponified with 1.3 ml of 3N sodium hydroxide solution, whereby 0.32 g of 4,4-dimethyl-2-oxo-5-hexenoic acid is obtained as a yellowish liquid.

3-(1-Phenyl-cyclobutyl)-2-oxo-propionic acid 10 g of 1-phenyl-cyclobutanecarbonitrile, dissolved in 70 ml of toluene, is mixed with 56 ml of diisobutylaluminum hydride in toluene (1.2 molar) at –72 to –69° C. After 4 hours at –75° C., 30 ml of ethyl acetate is added in drops. After heating to room temperature, additional ethyl acetate and water are added. It is filtered on diatomaceous earth, the organic phase is separated, dried ($Na_2SO_4$) and concentrated by evaporation. After chromatography on silica gel (hexane with 0–10% ethyl acetate), 7.6 g of 1-phenyl-cyclobutanecarbalde-hyde is obtained. 3 g of it is dissolved in 10 ml of tetrahydrofuran and added in drops at 0° C. to a solution, in which previously 5 g of triethyl-2-ethoxyphosphonoacetate in 70 ml of tetrahydrofuran was mixed at 0° C. with 10.3 ml of a 2 molar solution of lithium diisopropylamide in tetrahydro-furan/heptane/ethylbenzene. After 20 hours at room tempera-ture, water is added, it is extracted with ethyl acetate, dried ($Na_2SO_4$) and concentrated by evaporation. 2 g of this crude product is saponified with 28 ml of 1N sodium hydroxide solution. 1.32 g of the acid, which is heated for 20 hours to 90° C. with 25 ml of 1 molar sulfuric acid while being stirred vigorously, is obtained. After extraction with ether, drying ($Na_2SO_4$) and concentration by evaporation, 0.89 g of 3-(1-phenyl-cyclobutyl)-2-oxo-propionic acid is obtained as a yellowish oil.

3-[1-(2-Methoxyphenyl)-cyclopropyl]-2-oxo-propionic acid

Corresponding to J. Org. Chem. 40 (1975) 3497, 16.7 g of 2-methoxyphenylacetonitrile, 158 ml of lithium triisopropyl-amide (2 mol solution) and 46.7 ml of 1,2-dichloroethane in 96 ml of tetrahydrofuran and 58.6 ml of hexamethylphosphoric acid triamide are reacted with one another. 5.6 g of 1-(2-methoxy-phenyl)-cyclopropyl-carbonitrile, boiling point 104–115° C./0.1 mbar, which was also reacted as described for 3-(1-phenyl-cyclobutyl)-2-oxo-propionic acid, is obtained. 3-[1-(2-Methoxyphenyl)-cyclopropyl]-2-oxo-propionic acid is thus obtained as an oil.

Analogously to the process that is described for 3-(1-phenyl-cyclobutyl)-2-oxo-propionic acid and for 3-[1-(2- methoxyphenyl)-cyclopropyl]-2-oxo-propionic acid, the acids that are described in Table 2 were obtained.

TABLE 2

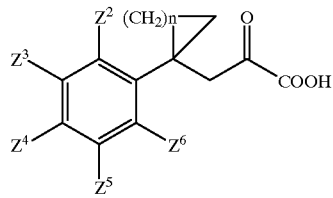

| Example | n | $Z^n$ ($\neq H$) | Melting Point (° C.) |
|---|---|---|---|
| | 1 | 3-F | oil |
| | 1 | 2-Cl | 60–63 |
| | 1 | 4-Cl | oil |
| | 1 | 2-Br | 49–54 |
| | 1 | 3-Br | oil |
| | 1 | 2,4-Cl$_2$ | 185–190 |
| | 1 | 3-OCH$_3$ | oil |
| | 1 | 3-CF$_3$ | oil |
| | 3 | | oil |
| | 3 | 4-CH$_3$ | 50–61 |
| | 4 | 4-OCH$_3$ | oil |

3-(1-Phenyl-cyclopropyl)-2-oxo-propionic acid is obtained analogously to the process that is described for 3-(1-phenyl-cyclobutyl)-2-oxo-propionic acid.

3-(1-Phenyl-cyclohexyl)-2-oxo-propionic acid is obtained analogously to the process that is described for 3-(1-phenyl-cyclobutyl)-2-oxo-propionic acid.

4-(3-Methoxyphenyl)-4-methyl-2-oxo-valeric acid 4.2 ml of a 0.6 m solution of 3-methoxyphenylmagnesium bromide in tetrahydrofuran is mixed at −70° C. with 257 mg of copper bromide-dimethylsulfide complex and then stirred at −40° C. for 20 minutes. It is cooled again to −70° C., and 0.33 ml of 1,3-dimethyl-tetrahydro-2-1H-pyrimidinone and a mixture of 400 mg of 4-methyl-2-oxo-3-pentenoic acid methyl ester (Liebigs Annalen [Liebigs Annals] 1974, 477) and 0.71 ml of trimethylchlorosilane in 3.5 ml of tetrahydrofuran are slowly added. It is stirred for one hour at −70° C. and then heated to room temperature. Then, 2N hydrochloric acid and ethyl acetate are added, the ethyl acetate phase is separated, it is concentrated by evaporation, and the residue is dissolved in 5 ml of dichloromethane. After 200 mg of tetrabutylammonium fluoride is added, it is left at room temperature for one hour, then washed with water, and the dichloromethane phase is dried (Na$_2$SO$_4$) and concentrated by evaporation. After chroma-tography on silica gel with hexane/ethyl acetate (97:3), 63 mg of 4-(3-methoxyphenyl)-4-methyl-2-oxo-valeric acid-methyl ester, which is mixed with 1 ml of potassium hydroxide in methanol (10%), is obtained. After 45 minutes, it is concentrated by evaporation, the residue is dissolved in water and extracted with diethyl ether. The aqueous phase is then acidified with 6N hydrochloric acid and extracted with diethyl ether. The diethyl ether phase is dried (Na$_2$SO$_4$) and concen-trated by evaporation. 50 mg of 4-(3-methoxyphenyl)-4-methyl-2-oxo-valeric acid is obtained.

2-Hydroxy-4-methyl-4-phenyl-2-trifluoromethyl-valeric acid

The Grignard reagent is produced from 1.5 g of magnesium and 10 g of 2-methyl-2-phenylpropyl chloride in 100 ml of diethyl ether, which yields 9.5 g of 2-hydroxy-4-methyl-4-phenyl-2-trifluoromethyl-valeric acid ethyl ester, boiling point 90° C./0.045 hPa, after reaction with 10 g of trifluoro-pyruvic acid ethyl ester.

7.5 g of the ethyl ester is refluxed with 100 ml of potassium hydroxide in methanol (10%) for 18 hours. After concentration by evaporation in a vacuum, the residue is dissolved in water and extracted with diethyl ether. The aqueous phase is acidified with 2N hydrochloric acid and extracted with diethyl ether. After the solvent is concentrated by evaporation, 3.2 g of 2-hydroxy-4-methyl-4-phenyl-2-trifluoromethyl-valeric acid is obtained as colorless crystals, boiling point 124–126° C.

4-(5-Fluoro-2-methoxyphenyl)-2-hydroxy-4-methyl-2-trifluoromethyl-valeric acid 1.3 g of anhydrous zinc chloride and 13.2 g of granular manganese are heated to boiling in 100 ml of tetrahydrofuran and boiled with 0.2 ml of methallyl bromide for 30 minutes. Then, the solution of 25 g of methallyl bromide and 17 g of trifluoropyruvic acid ethyl ester in 80 ml of tetrahydrofuran is added in drops at boiling heat over 2 hours, and boiled for another hour. Then, while being cooled with ice, saturated ammonium chloride solution and 300 ml of ethyl acetate are added, stirred for 30 minutes at 0° C., and the separated ethyl acetate phase is washed with saturated ammonium chloride solution and three times with water. The solvent is dried (Na$_2$SO$_4$) and concentrated by evaporation, and the residue is distilled in a vacuum. 17.6 g of 2-hydroxy-4-methylene-2-trifluoromethyl-valeric acid ethyl ester, boiling point 48° C./1 hPa, is obtained.

0.8 g of anhydrous aluminum chloride is added to 5 ml of 4-fluoranisole and 0.9 g of 2-hydroxy-4-methylene-2-trifluoromethyl-valeric acid ethyl ester. After 40 hours of stirring at room temperature, it is added to ice-cooled 2N hydrochloric acid and extracted with ethyl acetate. The ethyl acetate phase is washed with 1N hydrochloric acid and water, dried (Na$_2$SO$_4$) and concentrated by evaporation. After chromatography on silica gel with hexane/ethyl acetate (1:1), 1 g of 4-(5-fluoro-2-methoxyphenyl)-2-hydroxy-4-methyl-2-trifluoromethyl-valeric acid ethyl ester, melting point 38–39° C., is obtained.

1.9 g of 4-(5-fluoro-2-methoxyphenyl)-2-hydroxy-4-methyl-2-trifluoromethyl-valeric acid ethyl ester is refluxed with 40 ml of potassium hydroxide in methanol (10%) for 2 hours. After the solvent is concentrated by evaporation in a vacuum, water is added, it is extracted with hexane, and the separated water phase is acidified with 6N hydrochloric acid. After extraction with ethyl acetate, the ethyl acetate phase is washed with water, dried (Na$_2$SO$_4$) and concentrated by evaporation. The residue is crystallized from hexane. 1.55 g of 4-(5-fluoro-2-methoxyphenyl)-2-hydroxy-4-methyl-2-trifluoromethyl-valeric acid, melting point 102–104° C., is obtained.

2-Hydroxy-4-methyl-4-(2-thienyl)-2-trifluoromethyl-valeric acid and 2-hydroxy-4-methyl-4-(3-thienyl)-2-trifluoromethyl-valeric acid The mixture of 2-hydroxy-4-methyl-4-(2-thienyl)-2-trifluoromethyl-valeric acid and 2-hydroxy-4-methyl-4-(3-thienyl)-2-trifluoromethyl-valeric acid (9:1), melting point 150–151° C., was produced analogously.

The acids of Table 3 were produced analogously.

TABLE 3

Structure: phenyl ring with substituents Z², Z³, Z⁴, Z⁵, Z⁶ and side chain -C(CH₃)(CH₃)-CH₂-C(OH)(CF₃)-COOH

| $Z^n$ ($\neq H$) | Melting Point (° C.) |
|---|---|
| $Z^4 = CH_3$ | 136–138 |
| $Z^3 = Z^4 = CH_3$ | 115–117 |
| $Z^3 = Z^5 = CH_3$ | 118 |
| $Z^4 = Br$ | 131–132 |
| $Z^4 = Cl$ | 133–135 |
| $Z^4 = F$ | 140–141 |
| $Z^2 = OCH_3$ | 98–99 |
| $Z^4 = OCH_3$ | 129–130 |
| $Z^2 = Z^5 = OCH_3$ | 136–137 |
| $Z^2 = OCH_3, Z^5 = CH_3$ | 106–107 |
| $Z^2 = OCH_3, Z^4 = F$ | 103–106 |
| $Z^2 = OCH_3, Z^5 = F$ | 102–104 |
| $Z^4 = OCH_3, Z^2 = F$ | 122–124 |
| $Z^4 = OCH_3, Z^3 = F$ | 108–109 |
| $Z^2 = OCH_3, Z^5 = Cl$ | 103–105 |
| $Z^3/Z^4 = (CH_2)_3$ | 118–119 |
| $Z^3/Z^4 = -CH=CH-CH=CH-$ | 137 |
| $Z^2 = OCH_3, Z^4 = Br$ | 115–116 |
| $Z^2 = Br, Z^4 = OCH_3$ | 122–124 |
| $Z^4 = C_6H_5$ | 162–163 |
| $Z^2 = OCH_3, Z^4 = CH(CH_3)_2$ | 137–138 |

By conversion according to the standard process, additional acids are obtained from the acids above or their precursors:

2-Hydroxy-4-methyl-2-trifluoromethyl-4-(4-vinylphenyl)-valeric acid

By heating 4-(4-bromophenyl)-2-hydroxy-4-methyl-2-trifluoromethyl-valeric acid ethyl ester, tributylvinyltin, tri-o-tolylphosphine and bis-tri-o-tolylphosphine-palladium(II) chloride in dimethylformamide to 120° C., 2-hydroxy-4-methyl-2-trifluoromethyl-4-(4-vinylphenyl)-valeric acid ethyl ester, which provides the title compound, melting point 73–74° C., by alkaline saponification, is obtained.

4-(4-Acetylphenyl)-2-hydroxy-4-methyl-2-trifluoromethyl-valeric acid

Analogously to the compound above of 4-(4-bromophenyl)-2-hydroxy-4-methyl-2-trifluoromethyl-valeric acid ethyl ester, tributyl-1-ethoxyvinyltin, tri-o-tolylphosphine and bis-tri-o-tolylphosphine-palladium(II) chloride in dimethylformamide to 120° C. and subsequent acidic hydrolysis of the enol ether and alkaline saponification, melting point 158–162° C.

4-(4-Acetyl-3-methoxyphenyl)-2-hydroxy-4-methyl-2-trifluoromethyl-valeric acid

Analogously to the compound above of 4-(4-bromo-3-methoxyphenyl)-2-hydroxy-4-methyl-2-trifluoromethyl-valeric acid ethyl ester, tributyl-1-ethoxyvinyltin, tri-o-tolylphosphine and bis-tri-o-tolylphosphine-palladium(II) chloride in dimethylformamide to 120° C., oil.

4-(4-Cyanophenyl)-2-hydroxy-4-methyl-2-trifluoromethyl-valeric acid

From 4-(4-bromophenyl)-2-hydroxy-4-methyl-2-trifluoromethyl-valeric acid ethyl ester, zinc cyanide and tetrakis-triphenylphosphine-palladium in dimethylformamide at 140° C. After saponification, the title acid is obtained as a foam.

4-(4–Carbamoylphenyl)-2-hydroxy-4-methyl-2-trifluoromethyl-valeric acid is obtained by treating the ethyl ester of the acid above with hydrogen peroxide and saponification, melting point 244–245° C.

4-(4–Cyano-2-methoxyphenyl)-2-hydroxy-4-methyl-2-trifluoromethyl-valeric acid

From 4-(4-bromo-2-methoxyphenyl)-2-hydroxy-4-methyl-2-trifluoromethyl-valeric acid ethyl ester, zinc cyanide and tetrakis-triphenylphosphine-palladium in dimethylformamide at 140° C. After saponification, the title acid is obtained as an amorphous powder.

4-(3-Bromo-4-methoxyphenyl)-2-hydroxy-4-methyl-2-trifluoromethyl-valeric acid

From 2-hydroxy-4-(4-methoxyphenyl)-4-methyl-2-trifluoromethyl-valeric acid ethyl ester by bromation with N-bromosuccinimide in dimethylformamide at 0° C. and subsequent saponification. Melting point 94–96° C.

2-Hydroxy-4-methyl-4-(3-nitro-4-methoxyphenyl)-2-trifluoromethyl-valeric acid

This compound is obtained by reaction of 2.5 g of 2-hydroxy-4-(4-methoxyphenyl)-4-methyl-2-trifluoromethyl-valeric acid ethyl ester with 4 ml of 100% nitric acid in 12 ml of trifluoroacetic acid for one hour at 0° C., melting point 79–80° C.

4-(4-Iodo-2-methoxyphenyl)-4-methyl-2-oxo-valeric acid 3.2 g of 4-iodo-2-methoxybenzoic acid-methyl ester in 10 ml of diethyl ether is added to 24.2 mmol of methylmagnesium bromide in 23 ml of diethyl ether. After 20 hours, ammonium chloride solution is added, the ether phase is separated, dried and concentrated by evaporation. 2.4 g of the residue is dissolved in 10 ml of dichloromethane, mixed with 714 mg of 2-trimethylsilyloxy-acrylic acid-ethyl ester, cooled to −70° C. and mixed with 0.27 ml of tin(IV) chloride. After 15 minutes, the solution is added to potassium carbonate solution. After extraction with diethyl ether, the organic phase is washed with water, dried and concentrated by evaporation. 500 mg of the 4-(4-iodo-2-methoxyphenyl)-4-methyl-2-oxo-valeric acid ethyl ester that is thus obtained is stirred with 8.6 ml of 1 M sodium hydroxide in ethanol/water (2:1, v/v) for 3 hours at room temperature. After water is added, it is extracted with diethyl ether, the aqueous phase is acidified with 1 m hydrochloric acid and extracted with diethyl ether. After drying and concentration by evaporation, 410 mg of 4-(4-iodo-2-methoxyphenyl)-4-methyl-2-oxo-valeric acid is obtained as a yellowish oil.

4-(3-Chlorophenyl)-4-methyl-2-oxo-valeric acid is obtained analogously to the embodiment above of an amorphous powder.

4-(3-Bromophenyl)-4-methyl-2-oxo-valeric acid is obtained analogously to the embodiment above of an amorphous powder.

4-(2-Iodophenyl)-4-methyl-2-oxo-valeric acid is obtained analogously to the embodiment above as an amorphous powder.

4-(3-Iodophenyl)-4-methyl-2-oxo-valeric acid is obtained analogously to the embodiment above of an amorphous powder.

4-(4-Iodophenyl)-4-methyl-2-oxo-valeric acid is obtained analogously to the embodiment above as an oil.

4-(5-Fluoro-2-methoxyphenyl)-4-methyl-2-oxo-valeric acid is obtained analogously to the embodiment above, melting point 58–60° C.

4-(4-Bromo-2-methoxyphenyl)-2-oxo-valeric acid is obtained analogously to the embodiment above as an oil.

3-(1-Phenylcyclopentyl)-pyruvic acid is obtained analogously to the embodiment above from 1-phenylcyclopentanol with 2-trimethylsilyloxyacrylic acid-ethyl ester and tin(IV) chloride as an oil.

4-Toluenesulfonic acid-(2-hydroxy-4-phenyl-2-trifluoromethyl-pentyl)ester

A Grignard solution, to which 15 ml of oxalic acid diethyl ester is added at −30° C. within 30 minutes, is prepared from 2.6 g of magnesium chips and 15 ml of 2-phenyl-1-chloropropane in diethyl ether. It is stirred for one hour at −20° C. and for 2 hours at 0° C., and then mixed with saturated ammonium chloride solution. The diethyl ether phase is separated, dried ($Na_2SO_4$) and concentrated by evaporation and distilled in a vacuum. 17.7 g of 2-oxo-4-phenylvaleric acid ethyl ester, boiling point 98–100° C./0.03 hPa, is obtained.

4.4 g of 2-oxo-4-phenylvaleric acid ethyl ester is dissolved in 40 ml of tetrahydrofuran and mixed at −78° C. with 3.6 ml of trifluoromethyl-trimethylsilane and 2 ml of 1 M tetrabutylammonium fluoride in tetrahydrofuran. After 24 hours at −78° C., another 20 ml of 1 M tetrabutylammoinum fluoride in tetrahydrofuran is added. It is stirred for 1.5 hours at 0° C., ethyl acetate and saturated common salt solution are added, the organic phase is separated, and it is washed with saturated common salt solution and water. Then, it is dried ($Na_2SO_4$) and concentrated by evaporation and distilled on a bulb tube. 4.4 g of 2-hydroxy-4-phenyl-2-trifluoromethyl-valeric acid ethyl ester, boiling point 95–100° C./0.04 hPa, is obtained.

4.35 g of 2-hydroxy-4-phenyl-2-trifluoromethyl-valeric acid ethyl ester is dissolved in 100 ml of diethyl ether and stirred at 0° C. with 1.3 g of lithium aluminum hydride for one hour at 0° C. and for 16 hours at room temperature. A little water is added while being cooled, and it is stirred for one hour. The diethyl ether phase is separated, dried ($Na_2SO_4$) and concentrated by evaporation and distilled on a bulb tube. 4.1 g of 4-phenyl-2-trifluoromethyl-1,2-pentanediol, boiling point 120° C./0.04 hPa, is obtained.

4.25 g of 4-phenyl-2-trifluoromethyl-1,2-pentanediol in 30 ml of pyridine is mixed at 0° C. with 3.8 g of 4-toluenesulfonic acid chloride. After 16 hours at 0° C., it is concentrated by evaporation in a vacuum, mixed with ethyl acetate, washed with water, dried ($Na_2SO_4$) and concentrated by evaporation. By crystallization from ethyl acetate/hexane, 4.9 g of 4-toluenesulfonic acid-(2-hydroxy-4-phenyl-2-trifluoromethyl-pentyl)ester, melting point 95–96° C., is obtained.

Analogously, 4-toluenesulfonic acid-(2-hydroxy-4-methyl-4-phenyl-2-trifluoromethyl-pentyl)ester, melting point 78° C., is obtained.

Analogously, 4-toluenesulfonic acid-[4-(4-fluorophenyl)-2-hydroxy-4-methyl-2-trifluoromethyl-pentyl]ester, melting point 80–81° C., and 4-toluenesulfonic acid-[2-hydroxy-4-(2-methoxy-5-fluorophenyl)-4-methyl-2-trifluoromethyl-pentyl]ester, melting point 93–95° C., were produced.

2-(2-Phenylpropyl)-2-trifluoromethyl-oxiran 400 mg of 4-toluenesulfonic acid-(2-hydroxy-4-phenyl-2-trifluoromethyl-pentyl)ester in 5 ml of dimethylformamide is mixed at 0° C. with 35 mg of sodium hydride (80% in mineral oil). After one hour at 0° C., it is diluted with water and extracted with dichloromethane. The dichloromethane phase is washed with water, dried ($Na_2SO_4$) and concentrated by evaporation. The residue is distilled. 200 mg of 2-(2-phenylpropyl)-2-trifluoromethyl-oxiran, boiling point 110° C./1 hPa, is obtained.

4-Bromo-5-aminophthalide 23 g of 3-bromo-4-nitro-1,2-xylene is suspended in 200 ml of pyridine and 600 ml of water and mixed at 60° C. in portions with 260 g of potassium permanganate, whereby the temperature rises to 90° C. It is heated for 2 more hours to 95° C., filtered, the filtrate is acidified with hydrochloric acid and extracted with diethyl ether. After the solvent is concentrated by evaporation, 27 g of 3-bromo-4-nitrophthalic acid is obtained.

12 g of acid is heated for 15 minutes to 220° C. and then distilled on a bulb tube. At 0.03 hPa, 10 g of 3-bromo-4-nitrophthalic acid anhydride is distilled.

The anhydride is dissolved in 120 ml of dimethylformamide and is slowly mixed at 0° C. with 78.8 ml of a 0.5 M solution of sodium borohydride in dimethylformamide. After 3 hours at 0° C., 2N hydrochloric acid is carefully added, and it is extracted with ethyl acetate. After washing with potassium bicarbonate solution, drying ($Na_2SO_4$) and concentration by evaporation of the ethyl acetate phase, 6.6 g of 4-bromo-5-nitrophthalide is obtained.

6.6 g of 4-bromo-5-nitrophthalide is dissolved in 45 ml of ethanol and added in drops to a mixture of 65 g of iron(II) sulfate, 220 ml of water and 65 ml of ammonia (33%) that is heated to 60° C. and stirred well. After 2 hours at 60° C., the mixture is absorptively precipitated five times with 200 ml of diethyl ether. The diethyl ether phases are concentrated by evaporation. As a residue, 4.1 g of 4-bromo-5-aminophthalide is obtained, melting point 176–180° C.

6-Bromo-5-aminophthalide

4-Bromo-5-nitrophthalic acid anhydride is produced analogously to the process of 4-bromo-5-nitro-1,2-xylene that is described above.

By boiling with ethanol, a mixture of 2-bromo-6-ethoxycarbonyl-3-nitrobenzoic acid and 3-bromo-2-ethoxycarbonyl-4-nitrobenzoic acid is obtained from the above.

1.2 ml of oxalyl chloride is carefully added in drops to 7.2 ml of a 0.66 m solution of dimethylformamide in dichloromethane at 0° C. The solution is stirred for 1 hour at 0° C. and for 5 minutes at room temperature. After concentration by evaporation in a vacuum, the residue is suspended in 7 ml of acetonitrile, cooled to −35° C. and mixed drop by drop with 1.5 g of the ester mixture. After one hour at the same temperature, it is cooled to −70° C., and 2.4 ml of a 2 m solution of sodium borohydride in dimethylformamide is added in drops. It is stirred for 20 hours at room temperature, water is added, alkalized with potassium carbonate and extracted with diethyl ether. The diethyl ether phase is dried ($Na_2SO_4$) and concen-trated by evaporation. A mixture of 5-bromo-6-nitrophthalide and 6-bromo-5-nitrophthalide, which is separated on silica gel with hexane/ethyl acetate (95:5), is obtained.

The reduction to aminophthalide is carried out as described above. 6-Bromo-5-aminophthalide, melting point 235–241° C., is obtained.

5-Amino-3-(1-propenyl)-phthalide 5 g of 2-bromo-4-nitrobenzoic acid is converted into acid chloride, which is dissolved in 50 ml of tetrahydrofuran and added in drops to 3 ml of allylamine in 20 ml of tetrahydrofuran, by 2 hours of boiling with 30 ml of thionyl chloride and distilling-off of excess thionyl chloride. After 20 hours at room temperature, it is dispersed between 1N hydrochloric acid and ethyl acetate, the ethyl acetate phase is washed with water, dried ($Na_2SO_4$) and concentrated by evaporation. The residue is crystallized with hexane. 5.6 g of 2-bromo-4-nitrobenzoic acid-allylamide, melting point 98–100° C., is obtained.

This material is dissolved in 35 ml of ethanol and added in drops to a mixture of 50 g of iron(II) sulfate, 170 ml of water and 50 ml of ammonia (33%) that is heated to 60° C. and stirred well. After 2 hours at 60° C., the mixture is absorp-tively precipitated 5 times with 200 ml of diethyl ether, the diethyl ether phases are concentrated by evaporation, and the residue is crystallized with hexane. 3.1 g of 4-amino-2-bromo-benzoic acid-allylamide, melting point 115–117° C., is obtained.

11 g of 4-amino-2-bromobenzoic acid-allylamide, 5.2 ml of acetonylacetone and 200 mg of 4-toluenesulfonic acid are refluxed for 1.5 hours with a water separator. Then, the solution is diluted with ethyl acetate, washed with 1N hydrochloric acid and then with potassium carbonate solution, dried ($Na_2SO_4$) and concentrated by evaporation. The residue is crystallized with hexane. 13.4 g of N-allyl-2-bromo-4-(2,5-dimethylpyrrol-1-yl)-benzamide, melting point 136–138° C., is obtained.

3 g of N-allyl-2-bromo-4-(2,5-dimethylpyrrol-1-yl)-benzamide in 100 ml of dimethoxyethane is mixed at −70° C. with 14.2 ml of 1.4 M butyllithium in hexane. After 30 minutes at −70° C., 1.63 ml of crotonaldehyde is added. The solution is allowed to heat to room temperature, stirred for another 20 hours, 50 ml of 50% acetic acid is added and heated for 6 hours to 60° C. Then, it is diluted with water, extracted with ethyl acetate, the ethyl acetate phase is washed with potassium carbonate solution. The ethyl acetate phase is dried ($Na_2SO_4$) and concentrated by evaporation. After chromatography on silica gel with hexane ethyl acetate (98:2), the residue produces 1.1 g of crystalline 5-(2,6-dimethyl-pyrrol-1-yl)-3-(1-propenyl)-phthalide, melting point 91–95° C.

1.1 g of 5-(2,5-dimethylpyrrol-1-yl)-3-(1-propenyl)-phthalide, 8.56 g of hydroxylamine-hydrochloride and 4.58 g of potassium hydroxide in 75 ml of ethanol/water (16:6,8, vv) are heated for 24 hours at 120° C. The solvent is distilled off, the residue is mixed with water and extracted with ethyl acetate. The ethyl acetate phase is dried ($Na_2SO_4$) and concentrated by evaporation and chromatographed on silica gel. 640 mg of 5-amino-3-(1-propenyl)-phthalide, melting point 125–130° C., is obtained with dichloromethane/methanol (99:1).

The phthalides of Table 4 are obtained analogously.

TABLE 4

| $X^{3a}/X^{3b}$ | Melting Point [° C.] |
|---|---|
| $CH_3/H$ | 152–155 |
| $CH_3/CH_3$ | 94–97 |
| $C_2H_5/H$ | 137–140 |
| $C_2H_5/C_2H_5$ | 95–96 |
| $CH=CH_2/H$ | 89–93 |
| —$(CH_2)_4$— | 105–110 |

Analogously to the production of 4-bromo-5-(4-methyl-2-oxo-4-phenyl-valeroylamino)-phthalide, the compounds of Tables 5 and 6 are obtained.

TABLE 5

| Example | $Z^n$<br>Z ≠ H | Melting Point (° C.) |
|---|---|---|
| | $Z^2$ = I | 205–207 |
| | $Z^3$ = Cl | 170–171 |
| | $Z^3$ = Br | 168–169 |
| | $Z^3$ = I | 155–157 |

4-Bromo-5-(4-methyl-2-oxo-4-phenyl-valeroylamino)-phthalide 412 mg of 4-methyl-4-phenyl-2-oxovaleric acid is dissolved in 10 ml of dimethylacetamide and mixed under argon at −8° C. with 261 mg of thionyl chloride. After 20 minutes of stirring at −3 to +3° C., 228 mg of 4-bromo-5-aminophthalide is added. It is stirred for 1.5 hours at room temperature, then mixed with water, extracted with ethyl acetate, the organic phase is washed with water, dried ($Na_2SO_4$) and after the solvent is concentrated by evaporation and after treatment with diethyl ether, 360 mg of 4-bromo-5-(4-methyl-2-oxo-4-phenyl-valeroylamino)-phthalide, melting point 150–152° C, is obtained.

5-[3-(1-Phenyl-cyclopropyl)-2-oxo-propionylamino]-phthalide was obtained analogously to the process that is described for 4-bromo-5-(4-methyl-2-oxo-4-phenyl-valeroylamino)-phthalide from 5-aminophthalide and 3-(1-phenyl-cyclopropyl)-2-oxo-propionic acid, melting point 132–138° C.

5-[3-(1-Phenyl-cyclobutyl)-2-oxo-propionylamino]-phthalide was obtained analogously to the process that is described for 4-bromo-5-(4-methyl-2-oxo-4-phenyl-valeroylamino)- phthalide from 5-aminophthalide and 3-(1-phenyl-cyclobutyl)-2-oxo-propionic acid, melting point 142–146° C.

5-[3-(1-Phenyl-cyclohexyl)-2-oxo-propionylamino]-phthalide was obtained analogously to the process that is described for 4-bromo-5-(4-methyl-2-oxo-4-phenyl-valeroylamino)-phthalide from 5-aminophthalide and 3-(1-phenyl-cyclohexyl)-2-oxo-propionic acid, melting point 120–123° C.

The compounds of Table 6 were also produced:

TABLE 6

| Example | n | $Z^n$ (≠H) | Melting Point (° C.) |
|---|---|---|---|
| 1 | 1 | 3-F | 142–146 |
| | 1 | 2-Cl | 148–151 |
| | 1 | 4-Cl | 161–170 |
| | 1 | 2-Br | 172–178 |
| | 1 | 3-Br | 152–159 |
| | 1 | 2,4-Cl$_2$ | 135–138 |
| | 1 | 3-OCH$_3$ | 140–153 |
| | 1 | 3-CF$_3$ | 166–170 |
| | 3 | | 140–144 |
| | 3 | 4-CH$_3$ | oil |
| | 4 | 4-OCH$_3$ | 129–130 |

6-[3-(1-Phenyl-cyclopropyl)-2-oxo-propionylamino]-4-methyl-2,3-benzoxazin-1-one was obtained analogously to the process that is described for 4-bromo-6-(4-methyl-2-oxo-4-phenyl-valeroylamino)-phthalide from 6-amino-4-methyl-2,3-benzoxazin-1-one and 3-(1-phenyl-cyclopropyl)-2-oxo-propionic acid, melting point 197–200° C.

6-[3-(1-Phenyl-cyclobutyl)-2-oxo-propionylamino]-4-methyl-2,3-benzoxazin-1-one was obtained analogously to 6-[3-(1-phenyl-cyclopropyl)-2-oxo-propionylamino]-4-methyl-2,3-benzoxazin-1-one using 3-(1-phenyl-cyclobutyl)-2-oxo-propionic acid, melting point 155–156° C.

6-[3-(1-Phenyl-cyclohexyl)-2-oxo-propionylamino]-4-methyl-2,3-benzoxazin-1-one was obtained analogously to 6-[3-(1-phenyl-cyclopropyl)-2-oxo-propionylamino]-4-methyl-2,3-benzoxazin-1-one using 3-(1-phenyl-cyclohexyl)-2-oxo-propionic acid, melting point 132–134° C.

6-(4,4-Dimethyl-2-oxo-5-hexenoylamino)-phthalide was obtained analogously to the process that is described for 4-bromo-5-(4-methyl-2-oxo-4-phenyl-valeroylamino)-phthalide from 5-aminophthalide and 4,4-dimethyl-2-oxo-5-hexenoic acid, melting point 103–104° C.

6-Bromo-5-(4-methyl-2-oxo-4-phenyl-valeroylamino)-phthalide

Analogously to the example above, 1.7 g of 6-bromo-5-(4-methyl-2-oxo-4-phenyl-valeroylamino)-phthalide is obtained from 2.0 g of 4-methyl-4-phenyl-2-oxovaleric acid and 1.11 g of 6-bromo-5-aminophthalide with 1.27 g of thionyl chloride in 60 ml of dimethylacetamide, melting point 148–150° C.

5-[4-(4-Iodo-2-methoxyhenyl)-4-methyl-2-oxo-valeroylamino]-phthalide was obtained analogously to the process that is described for 4-bromo-5-(4-methyl-2-oxo-4-phenyl-valeroylamino)-phthalide from 5-aminophthalide and 4-(4-iodo-2-methoxyphenyl)-4-methyl-2-oxo-valeric acid as a foam.

5-[4-(4-Iodophenyl)-4-methyl-2-oxo-valeroylamino]-phthalide was obtained analogously to the process that is described for 4-bromo-5-(4-methyl-2-oxo-4-phenyl-valeroylamino)-phthalide from 5-aminophthalide and 4-(4-iodophenyl)-4-methyl-2-oxo-valeric acid as an oil.

5-[4-(3-Iodophenyl)-4-methyl-2-oxo-valeroylamino)-phthalide was obtained analogously to the process that is described for 4-bromo-5-(4-methyl-2-oxo-4-phenyl-valeroylamino)-phthalide from 5-aminophthalide and 4-(3-iodophenyl)-4-methyl-2-oxo-valeric acid, melting point 160–161° C.

5-[4-(4-Bromo-2-methoxyhenyl)-2-oxo-valeroylamino)-phthalide was obtained analogously to the process that is described for 4-bromo-5-(4-methyl-2-oxo-4-phenyl-valeroylamino)-phthalide from 5-aminophthalide and 4-(4-bromo-2-methoxyphenyl)-2-oxo-valeric acid, melting point 136–140° C.

5-[3-(1-Phenyl-cyclopentyl)-2-oxo-propionylamino]-phthalide was obtained analogously to the process that is described for 4-bromo-5-(4-methyl-2-oxo-4-phenyl-valeroylamino)-phthalide from 5-aminophthalide and 3-(1-phenyl-cyclopentyl)-2-oxo-propionic acid, melting point 140–144° C.

6-[4-(5-Fluoro-2-methoxyhenyl)-4-methyl-2-oxo-valeroylamino)-4-methyl-2,3-benzoxazin-1-one was obtained analogously to the process that is described for 4-bromo-5-94-methyl-2-oxo-4-phenyl-valeroylamino)-phthalide from 4-methyl-2,3-benzoxazin-1-one and 4-(5-fluoro-2-methoxyphenyl)-4-methyl-2-oxo-valeric acid, melting point 171–173° C.

6-[4-(5-Fluoro-2-methoxyhenyl)-4-methyl-2-oxo-valeroylamino)-4-ethyl-2,3-benzoxazin-1-one was obtained analogously to the process that is described for 4-bromo-5-(4-methyl-2-oxo-4-phenyl-valeroylamino)-phthalide from 4-ethyl-2,3-benzoxazin-1-one and 4-(5-fluoro-2-methoxyphenyl)-4-methyl-2-oxo-valeric acid, melting point 157–158° C.

6-Amino-4-methyl-2,3-benzoxazin-1-one 60 g of 2-methyl-5-nitroacetophenone, 38.5 g of 2,2-dimethyl-1,3-propanediol and 6 g of p-toluenesulfonic acid are boiled in 1 l of toluene with a water separator until water is no longer produced. The solution is washed with potassium bicarbonate, dried (Na$_2$SO$_4$) and concentrated by evaporation. 71.7 g of the crystalline ketal is obtained from pentane.

The latter is oxidized in 1.5 l of pyridine and 4.5 l of water with 350 g of potassium permanganate, as described above in the production of 4-bromo-5-aminophthalide. 56.4 g of 4-nitro-2-(2,5,5-trimethyl-1,3-dioxan-2-yl)-benzoic acid is obtained.

52 g of the acid is hydrogenated in 500 ml of methanol and 500 ml of ethyl acetate with 10 g of palladium/carbon (10%). 45.5 g of the crystalline amino compound is obtained from pentane.

10 g of the amine is refluxed with 100 ml of concentrated hydrochloric acid for 2 hours. The solvent is concentrated by evaporation in a vacuum, and the residue is refluxed with 15.7 g of hydroxylamine hydrochloride, 8.4 g of potassium hydroxide, 120 ml of ethanol and 50 ml of water for 12 hours. It is diluted with water, and the crystals are suctioned off. After drying, 3.5 g of 6-amino-4-methyl-2,3-benzoxazine-1-one, melting point 291–296° C., is obtained.

6-Amino-4-ethyl-2,3-benzoxazin-1-one is obtained analogously from 2-methyl-5-nitropropiophenone, melting point 89–93° C.

6-Amino- 1-methyl-1H-benzotriazole is described in Heterocycles 36, 259 (1993).

5-Amino-benz[1,2,5]oxadiazole is described in Boll. Sci. Fac. Chim. Ind. Bologna, 22, 33, 36, 37 (1964).

5-Amino-benz[1,2,5]-thiazole is described in J. Heterocycl. Chem. 11, 777 (1974).

5-Amino-1-indanone is described in J. Org. Chem. 27, 70 (1962).

6-Amino-1,2,3,4-tetrahydro-1-naphthalinone is described in J. Org. Chem. 27, 70 (1962).

6-Amino-3,4-dihydro-1H-2-benzopyran-1-one is produced by catalytic hydrogenation (palladium/carbon) in ethanol from the corresponding nitro compound (Canad. J. Chem. 61, 2643 (1983).

The examples below are used for a more detailed explanation of the invention. Other compounds can be produced by using homologous/analogous reagents. The required starting compounds are described above under "Starting Compounds."

EXAMPLE 1

Process 1

4-Bromo-5-(2-hydroxy-4-methyl-4-phenyl-2-trifluoromethyl-valeroylamino)-phthalide 350 mg of 4-bromo-5-(4-methyl-2-oxo-4-phenyl-valeroyl-amino)-phthalide is dissolved under argon in 15 ml of dimethylformamide and mixed with 0.77 ml of trifluoromethyl-trimethylsilane and 350 mg of cesium carbonate while being cooled with ice. After 3 hours of stirring at room tempera-ture, 5 ml of a 1 M solution of tetrabutylammonium fluoride in tetrahydrofuran and some drops of water are added and stirred for one hour at room temperature. After 100 ml of water is added, it is extracted with ethyl acetate, the organic phase is dried (Na$_2$SO$_4$) and concentrated by evaporation. 250 mg of 4-bromo-5-(2-hydroxy-4-methyl-4-phenyl-2-trifluoromethyl-valeroylamino)-phthalide, melting point 187–194° C., is obtained.

EXAMPLE 2

6-Bromo-5-(2-hydroxy-4-methyl-4-phenyl-2-trifluoromethyl-valeroylamino)-phthalide is obtained analogously to Example 1 from 1.6 g of 6-bromo-5-(4-methyl-2-oxo-4-phenyl-valeroylamino)-phthalide, 3.5 ml of trifluoromethyltrimethylsilane and 1.6 g of cesium carbonate, melting point 205–210° C.

EXAMPLE 3

5-(2-Hydroxy-4-methyl-2-pentafluoroethyl-4-phenyl-valeroylamino)-phthalide is obtained analogously to Example 1 from 20 mg of 5-(4-methyl-2-oxo-4-phenyl-valeroylamino)-phthalide, 0.1 ml of trimethyl-pentafluoroethylsilane and 20 mg of cesium carbonate, melting point 187–189° C.

EXAMPLE 4

5-[2-Hydroxy-4-(3-methoxyphenyl)-4-methyl-2-trifluoromethyl-valeroylamino]-phthalide is obtained analogously to Example 1 from 30 mg of 5-[4-(3-methoxyphenyl)-4-methyl-2-oxo-valeroylamino]-phthalide, 0.13 ml of trifluoromethyltrimethylsilane and 30 mg of cesium carbonate, melting point 173–178° C.

EXAMPLE 5

5-(2-Hydroxy-4,4-dimethyl-2-trifluoromethyl-5-hexenoylamino)-phthalide is obtained analogously to Example 1 from 200 mg of 5-(4,4-dimethyl-2-oxo-5-hexenoylamino)-phthalide, 0.22 ml of trifluoromethyl-trimethylsilane and 258 mg of cesium carbonate, melting point 153–157° C.

Analogously to Example 1, the compounds of Table 7 are obtained.

TABLE 7

| Example | n | Z$^n$ (≠H) | Melting Point (° C.) | Isomer |
|---|---|---|---|---|
| 6 | 1 | | 168–175 | Racemate |
| 7 | 1 | | 172–179 | (+)-Enantiomer |
| 8 | 1 | | 172–179 | (−)-Enantiomer |
| 9 | 1 | 3-F | 155–158 | Racemate |
| 10 | 1 | 2-Cl | 192–194 | Racemate |
| 11 | 1 | 4-Cl | 148–154 | Racemate |
| 12 | 1 | 4-Cl | 174–176 | (+)-Enantiomer |
| 13 | 1 | 4-Cl | 173–175 | (−)-Enantiomer |
| 14 | 1 | 2-Br | 163–165 | Racemate |
| 15 | 1 | 3-Br | 189–191 | Racemate |
| 16 | 1 | 2,4-Cl$_2$ | 216–218 | Racemate |
| 17 | 1 | 2-OCH$_3$ | 200–208 | (+)-Enantiomer |
| 18 | 1 | 2-OCH$_3$ | 195–208 | (−)-Enantiomer |
| 19 | 1 | 3-OCH$_3$ | 225–228 | Racemate |
| 20 | 1 | 3-CF$_3$ | 152–163 | Racemate |
| 21 | 2 | | 182–188 | Racemate |
| 22 | 2 | | 187–192 | (+)-Enantiomer |
| 23 | 2 | | 188–192 | (−)-Enantiomer |
| 24 | 3 | | 106–112 | (+)-Enantiomer |
| 25 | 3 | 4-CH$_3$ | 179–183 | Racemate |
| 26 | 4 | | 165–171 | Racemate |
| 27 | 4 | | 170–174 | (+)-Enantiomer |
| 28 | 4 | | 170–174 | (−)-Enantiomer |

If, instead of the aminophthalide, 6-amino-4-methylbenzoxazinone is used in Example 1, the compounds that are listed in Table 8 are obtained.

TABLE 8

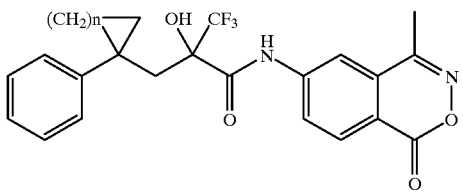

| Example | n | Melting Point (° C.) | Isomerism |
|---|---|---|---|
| 29 | 1 | 78–84 | racemate |
| 30 | 1 | 227–235 | (+)-enantiomer |
| 31 | 1 | 230–239 | (−)-enantiomer |
| 32 | 2 | 174–184 | racemate |
| 33 | 4 | 185–187 | racemate |
| 34 | 4 | 90–97 | (+)-enantiomer |
| 35 | 4 | 90–96 | (−)-enantiomer |

TABLE 9

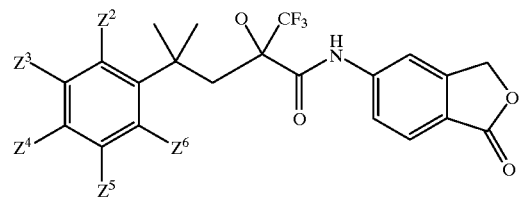

| Example | $Z^n$ (≠ H) | Melting Point (° C.) |
|---|---|---|
| 36 | $Z^2$ = 1 | amorphous |
| 37 | $Z^3$ = Cl | 174 |
| 38 | $Z^3$ = Br | 182–183 |
| 39 | $Z^3$ = I | 190–191 |

EXAMPLE 40

6-(2-Hydroxy-2,4-dimethyl4-phenyl-valeroylamino)-4-methyl-2,3-benzoxazin-1-one 72 mg of 6-(4-methyl4-phenyl-2-oxo-valeroylamino)-4-methyl-2,3-benzoxazin-1-one in 4 ml of tetrahydrofuran is mixed with 3 ml of methylmagnesium bromide (3 mol) at 0° C. After 30 minutes, ammonium chloride solution is added, the organic phase is separated, dried and concentrated by evaporation. After chromatography on silica gel (hexane/ethyl acetate 1:1), 39 mg of 6-(2-hydroxy-2,4-dimethyl4-phenyl-valeroylamino)-4-methyl-2,3-benzoxazin-1-one, melting point 173–175° C., is obtained.

EXAMPLE 41

Process 2

5-(2-Hydroxy-4-phenyl-2-trifluoromethyl-valeroylamino)-phthalide 500 mg of 2-hydroxy-4-phenyl-2-trifluoromethyl-valeric acid (Eur. Appl. 0 253 500 (Imperial Chemical Industries)) in 10 ml of dimethylacetamide is mixed at −15° C. with 0.14 ml of thionyl chloride. After 3 hours of stirring at −15° C., 600 mg of 5-aminophthalide (test) is added. The solution is stirred for 2 hours at −15° C. and then left for 18 hours at room temperature, then mixed with water and extracted with ethyl acetate. The ethyl acetate phase is dried ($Na_2SO_4$) and concentrated by evaporation. The residue is stirred with diethyl ether and suctioned off. 290 mg of 5-(2-hydroxy-4-phenyl-2-trifluoromethyl-valeroylamino)-phthalide, melting point 166–168° C., is obtained.

EXAMPLE 42

6-(2-Hydroxy-4-methyl-4-phenyl-2-trifluoromethyl-valeroyl-amino)-4-methyl-2,3-benzoxazin-1-one is obtained analogously to Example 41 from 784 mg of 2-hydroxy-4-phenyl-2-trifluoromethyl-valeric acid in 17 ml of dimethylacetamide and 500 mg of 6-amino-4-methyl-2,3-benzoxazin-1-one, melting point 172–173° C.

The compounds that are presented in Table 10 are produced analogously to Example 41:

TABLE 10

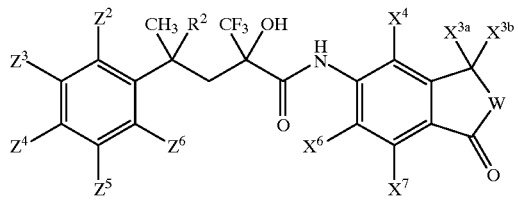

| Example | $R^2$ | W | $X^n$ (≠H) | $Z^n$ (≠H) | Melting point (° C.) | Isomerism or $[\alpha]_D$ (c = 0.5) (2) |
|---|---|---|---|---|---|---|
| 43 | H | O | $X^{3a}/X^{3b}$= H/$CH_3$ | | 175–185 | Diast. mixture |
| 44 | H | O | $X^{3a}$ = H, $X^{3b}$ = $CH_3$ | | 175–178 | +22.5 |
| 45 | H | O | $X^{3a}$ = H, $X^{3b}$ = $CH_3$ | | 210–213 | −74 |
| 46 | H | O | $X^{3a}$ = $CH_3$, $X^{3b}$ = H | | 210–213 | +69.5 |
| 47 | H | O | $X^{3a}$ = $CH_3$, $X^{3b}$ = H | | 175–179 | −21.5 |
| 48 | H | O | $X^{3a}$ = $C_2H_5$ | | 169–174 | |

TABLE 10-continued

[Structure diagram showing a compound with substituents $Z^2$, $Z^3$, $Z^4$, $Z^5$, $Z^6$, $CH_3$, $R^2$, $CF_3$, OH, $X^{3a}$, $X^{3b}$, $X^4$, $X^6$, $X^7$, W, and carbonyl/amide linkages]

| Example | $R^2$ | W | $X^n$ (≠H) | $Z^n$ (≠H) | Melting point (° C.) | Isomerism or $[\alpha]_D$ (c = 0.5) (2) |
|---|---|---|---|---|---|---|
| 49 | H | O | $X^{3a}$ = CH=CH$_2$ | | 162–174 | |
| 50 | H | O | $X^{3a}$ = CH=CH$_2$—CH$_3$ | | 160–162 | |
| 51 | H | O | $X^{3a}$ = CF$_3$ | | 156–166 | |
| 52 | H | O | $X^{3a}$ = $X^{3b}$ = CH$_3$ | | 160–171 | |
| 53 | H | O | $X^{3a}$ = $X^{3b}$ = C$_2$H$_5$ | | 172–176 | |
| 54 | H | O | $X^{3a}$ + $X^{3b}$ = (CH$_2$)$_4$ | | 168–170 | |
| 55 | H | O | $X^4$ = Br | | 180–185 | |
| 56 | CH$_3$ | O | | | 159–162 | |
| 57 | CH$_3$ | O | $X^4$ = Br | | 187–194 | |
| 58 | CH$_3$ | O | | $Z^2$ = CH$_3$ | 155–156 | racemate |
| 59 | CH$_3$ | O | | $Z^2$ = CH$_3$ | 148–149 | (+)-form |
| 60 | CH$_3$ | O | | $Z^2$ = CH$_3$ | 145–146 | (−)-form |
| 61 | CH$_3$ | O | | $Z^4$ = CH$_3$ | 189–190 | |
| 62 | CH$_3$ | O | | $Z^3$ = $Z^4$ = CH$_3$ | 206–207 | racemate |
| 63 | CH$_3$ | O | | $Z^3$ = $Z^4$ = CH$_3$ | 207–209 | (+)-form |
| 64 | CH$_3$ | O | | $Z^3$ = $Z^4$ = CH$_3$ | 207–209 | (−)-form |
| 65 | CH$_3$ | O | | $Z^3$ = $Z^5$ = CH$_3$ | 154 | racemate |
| 66 | CH$_3$ | O | | $Z^3$ = $Z^5$ = CH$_3$ | 188–189 | (+)-form |
| 67 | CH$_3$ | O | | $Z^3$ = $Z^5$ = CH$_3$ | 188 | (−)-form |
| 68 | CH$_3$ | O | | $Z^3/Z^4$ = (CH$_2$)$_3$ | 171–173 | |
| 69 | CH$_3$ | O | | $Z^3/Z^4$ = —CH=CH—CH=CH— | 218–219 | |
| 70 | CH$_3$ | O | | $Z^4$ = F | 177–178 | |
| 71 | CH$_3$ | O | | $Z^4$ = Cl | 184–185 | |
| 72 | CH$_3$ | O | | $Z^4$ = Br | 177–179 | |
| 73 | CH$_3$ | O | | $Z^2$ = OCH$_3$ | 134–135 | racemate |
| 74 | CH$_3$ | O | | $Z^4$ = OCH$_3$ | 183–184 | |
| 75 | CH$_3$ | O | | $Z^2$ = $Z^5$ = OCH$_3$ | 145 | |
| 76 | CH$_3$ | O | | $Z^2$ = OCH$_3$, $Z^5$ = CH$_3$ | 126–127 | racemate |
| 77 | CH$_3$ | O | | $Z^2$ = OCH$_3$, $Z^5$ = CH$_3$ | 169–170 | (+)-form |
| 78 | CH$_3$ | O | | $Z^2$ = OCH$_3$, $Z^5$ = CH$_3$ | 189 | (−)-form |
| 79 | CH$_3$ | O | | $Z^2$ = OCH$_3$, $Z^4$ = F | 180–181 | |
| 80 | CH$_3$ | O | | $Z^2$ = OCH$_3$, $Z^5$ = F | 140–141 | |
| 81 | CH$_3$ | O | | $Z^4$ = OCH$_3$, $Z^2$ = F | 207 | |
| 82 | CH$_3$ | O | | $Z^4$ = OCH$_3$, $Z^3$ = F | 178–179 | |
| 83 | CH$_3$ | O | | $Z^2$ = OCH$_3$, $Z^5$ = Cl | 141 | racemate |
| 84 | CH$_3$ | O | | $Z^2$ = OCH$_3$, $Z^6$ = Cl | 106–108 | +105.5 (1) |
| 85 | CH$_3$ | O | | $Z^2$ = OCH$_3$, $Z^5$ = Cl | 105–207 | −97 (1) |
| 86 | H | S | | | 189–191 | |
| 87 | CH$_3$ | S | | | 173–175 | |
| 88 | H | CH$_2$ | | | 161–162 | |
| 89 | H | O—CH$_2$ (3) | | | 192–195 | |
| 90 | CH$_3$ | O | | $Z^4$ = CH=CH$_2$ | 190–192 | racemate |
| 91 | CH$_3$ | O | | $Z^4$ = CN | 230–233 | racemate |
| 92 | CH$_3$ | O | | $Z^4$ = COCH$_3$ | 174–176 | racemate |
| 93 | CH$_3$ | O | | $Z^4$ = CONH$_2$ | 130–132 | racemate |
| 94 | CH$_3$ | O | | $Z^2$ = OCH$_3$, $Z^4$ = Br | 144–145 | racemate |
| 95 | CH$_3$ | O | | $Z^2$ = OCH$_3$, $Z^4$ = Br | 176–177 | (+)-enantiomer |
| 96 | CH$_3$ | O | | $Z^2$ = OCH$_3$, $Z^4$ = Br | 177–178 | −139.6 |
| 97 | CH$_3$ | O | | $Z^2$ = Br, $Z^4$ = OCH$_3$ | 197–198 | racemate |
| 98 | CH$_3$ | O | | $Z^2$ = OCH$_3$, $Z^4$ = CN | 135–136 | racemate |
| 99 | CH$_3$ | O | | $Z^3$ = NO$_2$, $Z^4$ = OCH$_3$ | 202–206 | racemate |
| 100 | CH$_3$ | O | | $Z^3$ = COCH$_3$, $Z^4$ = CH(CH$_3$)$_2$ | 135 | Racemate |
| 101 | CH$_3$ | O | | | 213–214 | Racemate |

(1) The optically active compounds that are presented in Table 10 were separated analogously to Example 88.
(2) In methanol.
(3) Formation of a 1-isochromanone.

EXAMPLE 102

(+) and (−) 5-[2-Hydroxy-4-methyl-4-(2-methoxyphenyl)-2-trifluoromethyl-valeroylamino]-phthalide The enantiomer mixture of Example 73 is separated by chromatography on chiral carrier material (CHIRALPAK AD$^{(R)}$, DAICEL Company) with hexane/2-propanol/ethanol (900:25:25, vvv). Thus, from 200 mg of racemate, there are obtained 73 mg of (−)-form, melting point 136–137° C., $[\alpha]_D$=−194.8° (c=0.5 in chloroform)

59 mg of (+)-form, melting point 135–136° C., $[\alpha]_D$=+192.2° (c=0.5 in chloroform).

EXAMPLE 103

5-[2-Hydroxy-4-methyl-4-(2-thienyl)-2-trifluoromethyl-valeroylamino]-phthalide and 5-[2-Hydroxy-4-methyl-4-(3-thienyl)-2-trifluoromethyl-valeroylamino]-phthalide The mixture of 2-hydroxy-4-methyl-4-(2-thienyl)-2-trifluoromethyl-valeric acid and 2-hydroxy-4-methyl-4-(3-thienyl)-2-trifluoromethyl-valeric acid (9:1) was reacted with 5-aminophthalide analogously to Example 41. After the position isomers are separated by chromatography and after the racemates are separated analogously to Example 58, there are obtained (+)-5-[2-hydroxy-4-methyl-4-(2-thienyl)-2-trifluoromethyl-valeroylamino]-phthalide, melting point 166° C., $[\alpha]_D$=+163.6° (c=0.5 in chloroform), (−)-5-[2-hydroxy-4-methyl-4-(2-thienyl)-2-trifluoromethyl-valeroylamino]-phthalide, melting point 166° C., $[\alpha]_D$=−160.8° (c=0.5 in chloroform), (+)-5-[2-hydroxy-4-methyl-4-(3-thienyl)-2-trifluoromethyl-valeroylamino]-phthalide, melting point 135° C. and (−)-5-[2-hydroxy-4-methyl-4-(3-thienyl)-2-trifluoromethyl-valeroylamino]-phthalide, melting point 135° C.

EXAMPLE 104

Process 3

5-(2-Hydroxy-4-phenyl-2-trifluoromethyl-pentylamino)-phthalide 760 mg of 5-acetamido-phthalide in 20 ml of dimethylformamide is mixed at 0° C. with 144 mg of sodium hydride (80% in mineral oil), and, after 20 minutes, with 800 mg of 4-toluenesulfonic acid-(2-hydroxy-4-phenyl-2-trifluoromethyl-pentyl)-ester. After 16 hours at 60° C., the solvent is concentrated by evaporation in a vacuum, the residue is dissolved in ethyl acetate, washed with water, dried (Na$_2$SO$_4$) and concentrated by evaporation. After chromatography on silica gel with cyclohexane/ethyl acetate (2:1), 266 mg of 5-(2-hydroxy-4-phenyl-2-trifluoromethyl-pentylamino)-phthalide, melting point 110° C., is obtained.

The compounds of Table 11 are obtained analogously to Example 104.

TABLE 11 (1)

| Example | R$^2$ | W | Z$^n$ (∼H) | Melting point (° C.) | Isomerization or $[\alpha]_D$ (c = 0.5) (2) |
|---|---|---|---|---|---|
| 105 | H | O | | 110 | racemate |
| 106 | H | O | | 123 | +18.6 |
| 107 | H | O | | 123 | −18.4 |
| 108 | CH$_3$ | O | | 139–140 | racemate |
| 109 | CH$_3$ | O | | 159–160 | +12.0 (4) |
| 110 | CH$_3$ | O | | 160–161 | −12.5 (4) |
| 111 | CH$_3$ | O | Z$^4$ = F | 148–149 | racemate |
| 112 | CH$_3$ | O | Z$^4$ = F | 162–164 | +9.0 |
| 113 | CH$_3$ | O | Z$^4$ = F | 162–164 | −6.7 |
| 114 | CH$_3$ | O | Z$^2$ = OCH$_3$, Z$^5$ = F | 148–149 | |
| 115 | H | CH$_2$ | | 161–162 | |
| 116 | H | OCH$_2$ (3) | | 127–128 | |

(1) The optically active compounds that are presented in Table 11 were separated analogously to Example 102.
(2) In methanol
(3) Formation of a 1-isochromanone.
(4) In chloroform.

EXAMPLE 117

4-Ethyl-6-(2-hydroxy-4-phenyl-2-trifluoromethyl-pentylamino)-2,3-benzoxazin-1-one The compound is obtained analogously to Example 104 from 151 mg of 6-acetamido-4-ethyl-2,3-benzoxazin-2-one, 208 mg of 4-toluenesulfonic acid-(2-hydroxy-4-phenyl-2-trifluoromethyl-pentyl)ester and 36 mg of sodium hydride, melting point 161–163° C.

EXAMPLE 118

1-(4-Nitro-3-trifluoromethylanilino)-4-phenyl-2-trifluoromethyl-2-pentanol 100 mg of 4-nitro-3-trifluoromethylacetanilide in 2 ml of dimethylformamide is mixed at 0° C. with 12 mg of sodium hydride (80% in mineral oil) and, after 20 minutes, with 150 mg of 2-(2-phenylpropyl)-2-trifluoromethyl-oxiran. It is stirred for 16 hours at 60° C., diluted with water and extracted with ethyl acetate. After washing with water, the ethyl acetate phase is dried (Na$_2$SO$_4$) and concentrated by evaporation. 80 mg of N-(2-hydroxy-4-methyl-4-phenyl-2-trifluoromethyl-valeroyl)-4-nitro-3-trifluoromethylaniline, melting point 119–120° C., is obtained.

After racemate separation analogously to Example 102, there are obtained the (−)-form, $[\alpha]_D$=−49.6° (c=0.5 in chloroform), the (+)-form, $[\alpha]_D$=+48.8° (c=0.5 in chloroform).

EXAMPLE 119

Process 4

6-(3-Hydroxy-3-methyl-1-butinyl)-5-(2-hydroxy-4-methyl-4-phenyl-2-trifluoromethyl-valeroylamino)-phthalide 150 mg of the bromine compound of Example 2 is dissolved together with 30 mg of 2-methyl-3-butin-2-ol, 0.24 mg of copper(I) iodide and 0.9 mg of triphenylphosphine in 1.5 ml of pyridine and mixed under argon with 0.25 mg of bis-triphenylphosphine-palladium(II) chloride. After 5 hours of reflux boiling, another 30 mg of 2-methyl-3-butin-2-ol is added, and it is refluxed for 20 hours. It is diluted with water and extracted with ethyl acetate. The ethyl acetate phase is dried ($Na_2SO_4$) and concentrated by evaporation. The crude product is chromatographed on silica gel. With cyclohexane/ethyl acetate (1:1), 60 mg of crystalline 6-(3-hydroxy-3-methyl-1-butinyl)-5-(2-hydroxy-4-methyl-4-phenyl-2-trifluoromethyl-valeroylamino)-phthalide, melting point 162–168° C., is obtained.

EXAMPLE 120

6-Acetyl-5-(2-hydroxy-4-methyl-4-phenyl-2-trifluoromethyl-valeroylamino)-phthalide 100 mg of the bromine compound of Example 2 is dissolved together with 95 mg of tributyl-(1-ethoxyvinyl)-tin and 8 mg of bis-triphenylphosphine-palladium(II) chloride in 4 ml of toluene under argon. After 5 hours of reflux boiling, another 45 mg of bis-triphenylphosphine-palladium(II) chloride is added, and it is refluxed for 20 hours. 1N hydrochloric acid is added and extracted with ethyl acetate. The ethyl acetate phase is dried ($Na_2SO_4$) and concentrated by evaporation. The crude product is stirred in 3 ml of tetrahydrofuran and 3 ml of 2N hydrochloric acid for 2 days at room temperature. It is mixed with water and extracted with ethyl acetate. After washing with water, it is dried ($Na_2SO_4$) and concentrated by evaporation. The residue is pulverized with diethyl ether/pentane, and 21 mg of crystalline 6-acetyl-5-(2-hydroxy-4-methyl-4-phenyl-2-trifluoromethyl-valeroylamino)-phthalide, melting point 195–199° C., is obtained.

The compounds of Table 12 are obtained analogously to Examples 119 and 120.

TABLE 12

| Example | $X^n$ (≠H) | $Z^n$ (≠H) | Melting Point (° C.) |
|---|---|---|---|
| 121 | $X^4$ = CH=$CH_2$ | | foam |
| 122 | $X^6$ = CH=$CH_2$ | | 191–197 |
| 123 | $X^6$ = C(O$C_2H_5$)=$CH_2$ | | 160–163 |
| 124 | $X^6$ = C≡C—$CH_2$OH | | 208–211 |
| 125 | $X^6$ = $C_6H_5$ | | 160–163 |
| 126 | $X^6$ = (1-ethynylcyclohexan-1-ol) | | 157–158 |
| 127 | $X_6$ = $C_6H_4OCH_3$(p-) | | 125–127 |
| 128 | | $Z^3$ = CH=$CH_2$ | 178–180 |
| 129 | | $Z^3$ = $C_2H_5$(*) | 152–153 |
| 130 | | $Z^3$ = $COCH_3$(**) | 220 |
| 131 | | $Z^3$ = CN | 112 |
| 132 | | $Z^4$ = CH=$CH_2$ | 190–192 |
| 133 | | $Z^4$ = $COCH_3$ | 205–207 |

(*) Obtained from the vinyl compound by catalytic hydrogenation.
(**) Obtained from the enol ether by mild acidic hydrolysis.

EXAMPLE 134

Process 5

5-[4-(3-Fluoro-4-hydroxyphenyl)-2-hydroxy-4-methyl-4-2-trifluoromethyl-valeroylamino]-phthalide 132 mg of 5-[4-(3-fluoro-4-methoxyphenyl)-2-hydroxy-4-methyl-4-2-trifluoromethyl-valeroylamino]-phthalide (Example 50) is dissolved in 15 ml of dichloromethane and mixed at 0° C. with 1.2 ml of a 1 M solution of boron tribromide in dichloromethane. After 16 hours at 0° C., ice, ethyl acetate and potassium bicarbonate are added to the mixture, and the ethyl acetate phase is separated, dried ($Na_2SO_4$) and concentrated by evaporation. 120 mg of 5-[4-(3-fluoro-4-hydroxyphenyl)-2-hydroxy-4-methyl-4-2-trifluoromethyl-valeroylamino]-phthalide, melting point 139–140° C., is obtained from ethyl acetate/diisopropyl ether/hexane.

The compounds that are presented in Table 13 are obtained analogously to Example 134.

TABLE 13 (1)

| Example | B | $Z^n$ (~H) | Melting Point (° C.) | Isomerization or $[\alpha]_D$ (c = 0.5) (2) |
|---|---|---|---|---|
| 135 | C=O | $Z^2$ = OH | 222–224 | |
| 136 | C=O | $Z^4$ = OH | 228–230 | |
| 137 | C=O | $Z^2$ = $Z^5$ = OH | 265–267 | |
| 138 | C=O | $Z^2$ = OH, $Z^5$ = $CH_3$ | 215–217 | racemate |
| 139 | C=O | $Z^2$ = OH, $Z^5$ = $CH_3$ | 173–174 | (+)-form |
| 140 | C=O | $Z^2$ = OH, $Z^5$ = $CH_3$ | 173–174 | (−)-form |
| 141 | C=O | $Z^2$ = OH, $Z^4$ = F | 240–242 | |
| 142 | C=O | $Z^2$ = OH, $Z^5$ = F | 201–202 | |
| 143 | C=O | $Z^4$ = OH, $Z^2$ = F | 242–243 | |
| 144 | C=O | $Z^2$ = OH, $Z^5$ = Cl | 220–221 | |
| 145 | $CH_2$ | $Z^2$ = OH, $Z^5$ = F | 156–157 | racemate |
| 146 | $CH_2$ | $Z^2$ = OH, $Z^5$ = F | 157–159 | +23.5 |
| 147 | $CH_2$ | $Z^2$ = OH, $Z^5$ = F | 157–159 | −18.7 |

TABLE 13 (1)-continued

Structure: Z²,Z³,Z⁴,Z⁵,Z⁶-substituted phenyl with HO, CF₃, B-N linked to isobenzofuranone

| Example | B | $Z^n$ (~H) | Melting Point (° C.) | Isomerization or $[\alpha]_D$ (c = 0.5) (2) |
|---|---|---|---|---|
| 148 | C=O | $Z^2$ = OH, $Z^4$ = Br | 224–226 | racemate |
| 149 | C=O | $Z^3$ = NO₂, $Z^4$ = OH | 167–169 | racemate |
| 150 | C=O | $Z^3$ = Cl, $Z^4$ = OH | 168–169 | racemate |
| 151 | C=O | $Z^3$ = Br, $Z^4$ = OH | 105 | racemate |

(1) The optically active compounds that are presented in Table 13 were separated analogously to Example 102.
(2) In methanol.

EXAMPLE 152

5-[4-(3-Fluorophenyl)-2-hydroxy-4-methyl-4-2-trifluoromethyl-valeroylamino]-phthalide 66 mg of (3-fluoro-4-hydroxyphenyl)-2-hydroxy-4-methyl-4-2-trifluoromethyl-valeroylamino]-phthalide is stirred with 126 mg of potassium carbonate and 108 mg of 5-chloro-1-phenyl-1H-tetrazole in 3 ml of dimethylformamide for 16 hours. Then, the dimethylformamide is distilled off in a vacuum, and the residue is dispersed between 1N hydrochloric acid and ethyl acetate. After washing with water, the ethyl acetate phase is dried (Na₂SO₄) and concentrated by evaporation, and the residue is chromatographed on silica gel with hexane/ethyl acetate (1:1). The product is hydrogenated in 10 ml of methanol with 30 mg of palladium/carbon (10%). After the catalyst is removed and the solvent is concentrated by evaporation, the product is chromatographed on silica gel with hexane/ethyl acetate (1:1). 49 mg of 5-[4-(3-fluorophenyl)-2-hydroxy-4-methyl-4-2-trifluoromethyl-valeroylamino]-phthalide, melting point 157° C., is obtained.

By racemate cleavage analogously to Example 102, the (+)-form is obtained with melting point 140–141° C., and the (−)-form is obtained with melting point 141° C.

EXAMPLE 153

5-[2-Hydroxy-4-methyl-4-(3-tolyl)-2-trifluoromethyl-valeroylamino]-phthalide

The compound is produced analogously to the example above from 57 mg of 5-[2-hydroxy-4-(2-hydroxy-5-methylphenyl)-4-methyl-2-trifluoromethyl-valeroylamino]-phthalide, melting point 152–153° C.

By racemate cleavage analogously to Example 102, the (+)-form is obtained with melting point 148–149° C., and the (−)-form is obtained with melting point 145–146° C.

EXAMPLE 154

5-[4-(5-Fluoro-2-ethoxyphenyl)-2-hydroxy-4-methyl-4-2-trifluoromethyl-valeroylamino]-phthalide 44 mg of 5-[4-(5-fluoro-2-hydroxyphenyl)-2-hydroxy-4-methyl-4-2-trifluoromethyl-valeroylamino]-phthalide is stirred in 1 ml of dimethylformamide with 28 mg of potassium carbonate and 50 mg of ethyl iodide for 24 hours at room temperature. It is then mixed with water, extracted with ethyl acetate, the organic phase is washed with water, dried (Na₂SO₄) and after the solvent is concentrated by evaporation, 35 mg of 5-[4-(5-fluoro-2-ethoxyphenyl)-2-hydroxy-4-methyl-4-2-trifluoromethyl-valeroylamino]-phthalide, melting point 108° C., is obtained.

Analogously to Example 154, the compounds of Table 14 were produced:

TABLE 14

Structure: 2-OR, 5-F substituted phenyl with OH, CF₃, amide linked to isobenzofuranone

| Example | R | Melting Point (° C.) | Isomerism or $[\alpha]_D$ (c = 0.5) (2) |
|---|---|---|---|
| 155 | CH(CH₃)₂ | 153–154 | racemate |
| 156 | CH₂CH=CH₂ | 152 | racemate |
| 157 | CH₂CH=CH₂ | 187–189 | racemate |
| 158 | CH₂CN | 170–172 | racemate |
| 159 | CH₂COOC(CH₃)₃ | 145 | racemate |
| 160 | CH₂COOC(CH₃)₃ | 143 | −131.5 |
| 161 | CH₂COOC(CH₃)₃ | 142–143 | (+)-form |

EXAMPLE 162

5-[4-(3-Chloro-4-methoxyphenyl)-2-hydroxy-4-methyl-2-trifluoromethyl-valeroylamino)-phthalide 22 mg of 5-[2-hydroxy-4-(4-methoxyphenyl)-4-methyl-2-trifluoromethyl-valeroylamino]-phthalide is stirred in 1.5 ml of methanol with 20 mg of N-chlorosuccinimide for 5 hours. The mixture is then dispersed in ice water, sodium bicarbonate solution and ethyl acetate, the ethyl acetate phase is dried, and it is concentrated by evaporation. 20 mg of 5-[4-(3-bromo-4-methoxyphenyl)-2-hydroxy-4-methyl-2-trifluoromethyl-valeroylamino]-phthalide, which melts after recrystallization from isopropyl ether at 189–191° C., is thus obtained.

5-[4-(3–Chloro-4-hydroxyphenyl)-2-hydroxy-4-methyl-2-trifluoromethyl-valeroylamino]-phthalide is obtained from 5-[4-(3-chloro-4-methoxyphenyl)-2-hydroxy-4-methyl-2-trifluoromethyl-valeroylamino]-phthalide by ether cleavage analogously to Example 134, melting point 105° C.

The 2,3-benzoxazinone and phthalazinone derivatives of Table 15 were produced according to the above-mentioned processes.

TABLE 15

| Example | $R^2$ | V | $Z^n$ ($\neq$H) | B | $Y^n$ ($\neq$H) | Melting point (° C.) | Isomerization or $[\alpha]_D$ (c = 0.5) (2) |
|---|---|---|---|---|---|---|---|
| 163 | H | O | | C=O | $Y^4 = CH_3$ | 165–166 | Racemate |
| 164 | H | O | | C=O | $Y^4 = C_2H_5$ | 159–160 | Racemate |
| 165 | $CH_3$ | O | | C=O | $Y^4 = CH_3$ | 185 | +162 |
| 166 | $CH_3$ | O | | C=O | $Y^4 = CH_3$ | 184–185 | −182 |
| 167 | $CH_3$ | O | | C=O | $Y^4 = C_2H_{5R}$ | 148–153 | Racemate |
| 168 | $CH_3$ | O | | C=O | $Y^4 = C_2H_5$ | 159–160 | +173 |
| 169 | $CH_3$ | O | | C=O | $Y^4 = C_2H_5$ | 159–160 | −175 |
| 170 | $CH_3$ | O | $Z^2 = OCH_3$ | C=O | $Y^4 = CH_3$ | 161–163 | Racemate |
| 171 | $CH_3$ | O | $Z^2 = OCH_3$ | C=O | $Y^4 = CH_3$ | 173–175 | −54.7 (4) |
| 172 | $CH_3$ | O | $Z^2 = OCH_3$ | C=O | $Y^4 = CH_3$ | 173–175 | (+)-Form |
| 173 | $CH_3$ | O | $Z^2 = OCH_3$ | C=O | $Y^4 = C_2H_5$ | 164 | Racemate |
| 174 | $CH_3$ | O | $Z^2 = OCH_3$ | C=O | $Y^4 = C_2H_5$ | 190–191 | (+)-Form |
| 175 | $CH_3$ | O | $Z^2 = OCH_3$ | C=O | $Y^4 = C_2H_5$ | 190–191 | −161.3 (CHCl$_3$) |
| 176 | $CH_3$ | O | $Z^2 = OCH_3, Z^5 = F$ | C=O | $Y^4 = CH_3$ | 165 | Racemate |
| 177 | $CH_3$ | O | $Z^2 = OCH_3, Z^5 = F$ | C=O | $Y^4 = CH_3$ | 188–189 | (+)-Form |
| 178 | $CH_3$ | O | $Z^2 = OCH_3, Z^5 = F$ | C=O | $Y^4 = CH_3$ | 187–188 | −132.8(CHCl$_3$) |
| 179 | $CH_3$ | O | $Z^2 = OCH_3, Z^5 = F$ | C=O | $Y^4 = C_2H_5$ | 126–128 | Racemate |
| 180 | $CH_3$ | O | $Z^2 = OCH_3, Z^5 = F$ | C=O | $Y^4 = C_2H_5$ | 170–171 | −147.4 |
| 181 | $CH_3$ | O | $Z^2 = OCH_3, Z^5 = F$ | C=O | $Y^4 = C_2H_5$ | 171 | (+)-Form |
| 182 | $CH_3$ | O | $Z^2 = OCH_3, Z^5 = Cl$ | C=O | $Y^4 = CH_3$ | 182–184 | Racemate |
| 183 | $CH_3$ | O | $Z^2 = OCH_3, Z^5 = Cl$ | C=O | $Y^4 = CH_3$ | 198–199 | (+)-Form |
| 184 | $CH_3$ | O | $Z^2 = OCH_3, Z^5 = Cl$ | C=O | $Y^4 = CH_3$ | 197–198 | −90.2 |
| 185 | $CH_3$ | O | $Z^2 = OCH_3, Z^4 = Br$ | C=O | $Y^4 = CH_3$ | 206–207 | Racemate |
| 186 | $CH_3$ | O | $Z^2 = OCH_3, Z^4 = Br$ | C=O | $Y^4 = CH_3$ | 194–198 | (+)-Form |
| 187 | $CH_3$ | O | $Z^2 = OCH_3, Z^4 = Br$ | C=O | $Y^4 = CH_3$ | 196–198 | −122.2 (CHCl$_3$) |
| 188 | $CH_3$ | O | $Z^4 = CH_3$ | C=O | $Y^4 = CH_3$ | 222–223 | Racemate |
| 189 | $CH_3$ | O | $Z^4 = CH_3$ | C=O | $Y^4 = C_2H_5$ | 187–188 | Racemate |
| 190 | $CH_3$ | O | $Z^4 = CH_3$ | C=O | $Y^4 = C_2H_5$ | 160 | −63.7 |
| 191 | $CH_3$ | O | $Z^4 = CH_3$ | C=O | $Y^4 = C_2H_5$ | 160 | (+)-Form |
| 192 | $CH_3$ | O | $Z^4 = F$ | C=O | $Y^4 = CH_3$ | 188–190 | Racemate |
| 193 | $CH_3$ | O | $Z^4 = Br$ | C=O | $Y^4 = CH_3$ | 219–220 | Racemate |
| 194 | $CH_3$ | O | $Z^4 = Br$ | C=O | $Y^4 = CH_3$ | 231–233 | −49.3 |
| 195 | $CH_3$ | O | $Z^4 = Br$ | C=O | $Y^4 = CH_3$ | 231–233 | (+)-form |
| 196 | $CH_3$ | O | | C=O | $Y^4 = CF_3$ | 175–183 | |
| 197 | $CH_3$ | NH | | C=O | $Y^4 = CH_3$ | | |
| 198 | $CH_3$ | $NCH_3$ | | C=O | $Y^4 = CH_3$ | | |
| 199 | $CH_3$ | O | $Z^2 = OH, Z^5 = F$ | C=O | $Y^4 = CH_3$ | 234–236 | Racemate |
| 200 | $CH_3$ | O | $Z^2 = OH, Z^5 = F$ | C=O | $Y^4 = CH_3$ | 232–234 | (+)-Form |
| 201 | $CH_3$ | O | $Z^2 = OH, Z^5 = F$ | C=O | $Y^4 = CH_3$ | 232–234 | −34.1 |
| 202 | $CH_3$ | O | $Z^2 = OH, Z^4 = Br$ | C=O | $Y^4 = CH_3$ | 248–250 | Racemate |
| 203 | $CH_3$ | O | $Z^3 = NO_2, Z^4 = OCH_3$ | C=O | $Y^4 = CH_3$ | 215–217 | Racemate |
| 204 | $CH_3$ | O | | $CH_2$ | $Y^4 = CH_3$ | 148–149 | Racemate |
| 205 | $CH_3$ | O | | $CH_2$ | $Y^4 = CH_3$ | 132–133 | Racemate |
| 206 | $CH_3$ | O | | $CH_2$ | $Y^4 = C_2H_5$ | 121–122 | Racemate |

(1) The optically active compounds that are presented in Table 15 were separated analogously to Example 102.
(2) In methanol.
(4) In chloroform.

EXAMPLE 207

5-(2-Hydroxy-4-phenyl-2-trifluoromethyl-valeroylamino)-benz[1,2,5]oxadiazole

The compound was obtained from 2-hydroxy-4-phenyl-2-trifluoromethyl-valeric acid and 5-amino-benz[1,2,5]oxadiazole analogously to Example 41. Melting point 192° C.

EXAMPLE 208

5-(2-Hydroxy-4-phenyl-2-trifluoromethyl-valeroylamino)-benzo[1,2,5]thiadiazole

The compound was obtained from 2-hydroxy-4-phenyl-2-trifluoromethyl-valeric acid and 5-amino-benzo[1,2,5]thiadiazole analogously to Example 41. Melting point 166–167° C.

EXAMPLE 209

6-(2-Hydroxy-4-phenyl-2-trifluoromethyl-valeroylamino)-1-methyl-benzotriazole

The compound was obtained from 2-hydroxy-4-phenyl-2-trifluoromethyl-valeric acid and 6-amino-1-methyl-benzotriazole analogously to Example 41. Melting point 194–196° C.

What is claimed is:

1. A compound of formula I

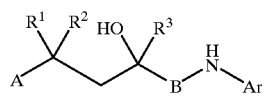

in which

- $R^1$ and $R^2$ are the same or different and each stands for a hydrogen atom, a $C_1$–$C_5$, alkyl, or a halogen atom, or $R^1$ and $R^2$ together with the C-atom of the chan form a 3–7-membered ring;
- $R^3$ stands for a $C_1$–$C_5$ alkyl group or a partially or completely fluorinated $C_1$–$C_5$ alkyl group;
- A stands for a monocyclic or bicyclic, carbocylic or heterocyclic, aromatic ring that is optionally substituted by one or more radicals, selected from halogen atoms, $C_1$–$C_5$ alkyl groups,
  $C_2$–$C_5$ alkenyl groups -$CR^5$=$CR^6R^7$,
  hydroxy groups, or
  hydroxy groups that carry a $C_1$–$C_{10}$ acyl group, a $C_3$–$C_{10}$ carbalkoxyalkyl group, a $C_2$–$C_5$ cyanalkyl group, a $C_3$–$C_{10}$ unsubstituted or substituted allyl group, a $C_3$–$C_{10}$ unsubstituted or substituted propargyl group, a $C_2$–$C_5$ alkoxyalkyl gorup, a $C_1$–$C_5$ alkyl group that is partially or completely substituted by fluorine atoms,
  a cyano group,
  a nitro group,
  $C_1$–$C_5$ alkoxy groups,
  $C_1$–$C_5$ alkyltho groups,
  mono- or disubstituted $C_1$–$C_{10}$ amino groups, or partially or completely fluorinated $C_1$–$C_5$ alkyl groups;
- A may also stand for an ester group -$COOR^4$, a $C_2$–$C_5$ alkenyl group -$CR^{5'}$=$CR^{6'}R^{7'}$, an alkynyl group -C≡$CR^5$, or a partially or completely fluorinated $C_1$–$C_5$ alkyl group;
- $R^4$ is a $C_1$–$C_5$ alkyl group:
- $R^5, R^6$ and $R^7$ are the same or different and, independently of one another, are each hydrogen atoms or $C^1$–$C^5$ alkyl groups;
- $R^{5'}, R^{6'}$ and $R^{7'}$ are the same or different, and, independently of one another, mean hydrogen atoms, halogen atoms, aryl radical or $C_1$–$C_5$ alkyl groups;
- B stands for a carbonyl group or a $CH_2$ group; and
- Ar stands for a ring system, selected from the group of partial formulas 5 and 8,

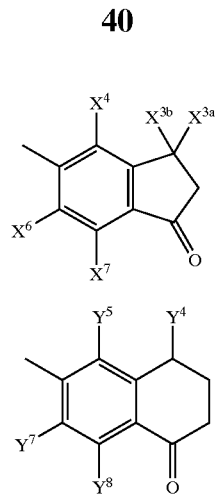

in which radicals $X^{3a}$, $X^{3b}$, $X^4$, $X^6$, $X^7$, $Y^4$, $Y^5$, $Y^7$ and $Y^8$ are each the same or different and are selected from hydrogen atoms $C_1$–$C_5$ alkyl groups, which in addition may contain a hydroxy group that is optionally etherified with a $C_1$–$C_5$ alkyl group or esterified with a $C_1$–$C_5$ alkanoyl group, partially or completely fluorinated $C_1$–$C_5$ alkyl groups, $C_2$–$C_5$ alkenyl groups -$CR^5$=$CR^6R^7$, alkynyl groups -C≡$CR^5$, radicals $X^{3a}$ and $X^{3b}$ also together with the C-atom of benzocondensed ring system of partial formula 5 may form a 3–7 membered ring, and radicals $X^4$, $X^6$, $X^7$, $Y^4$, $Y^5$, $Y^7$, $Y^8$ in partial formulas 5 and 8 may also be selected from halogen atoms, hydroxy groups, $C_1$–$C_5$ alkoxy groups or $C_1$–$C_5$ alkanoyloxy groups; also, if B in general formula I is a $CH_2$ group, Ar can also be a phenyl radical of partial formula 12,

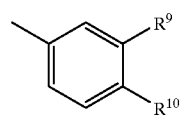

in which $R^9$ and $R^{10}$ are the same or different and mean a cyano group, a nitro group, a halogen atom, a $C_1$–$C_5$ alkyl group, a partially or completely fluorinated $C_1$–$C_5$ alkyl group, a $C_1$–$C_5$ alkylthio group, a $C_1$–$C_5$ alkylsulfinyl group or a $C_1$–$C_5$ alkylsylfonyl group; or if B stands for a $CH_2$ group, a physiologically compatible salt of a compound of formula I.

2. A compound according to claim 1, wherein said comopund is in the form of a racemate or diastereomer mixture.

3. A compound according to claim 1, wherein said comound is in the form of a separate optical isomer.

4. A compound according to claim 1, wherein $R_1$ and $R_2$ are the same or different and each stand for a hydrogen atom, methyl or ethyl, or $R_1$ and $R_2$ together with the C-atom to which they are attached form a cyclopropyl ring.

5. A compound according to claim 1, wherein $R^3$ stands for a $C_1$–$C_5$ perfluoroalkyl group.

6. A compound according to claim 1, wherein A stands for a benzene, naphthalene or thiophene ring, which in each case is optionally substituted by one or more radicals, selected from fluorine atoms, chlorine atoms, bromine atoms, methyl groups, ethyl groups, vinyl groups, hydroxy groups, methoxy groups, ethoxy groups and $(CH_2)_n$ groups, in which n is 3, 4 or 5, wherein that $(CH_2)_n$ groups form a ring of n+2 carbon atoms which optionally contains saturations.

7. A compound according to claim 1, wherein $X^{3a}$ stands for a hydrogen atom or a $C_1$–$C_5$ alkyl group.

8. A compound according to claim 1, wherein $X^{3a}$ and $X^{3b}$ are the same or different and stand for a hydrogen atom or a $C_1$–$C_5$ alkyl group.

9. A compound according to claim 1, wherein $X^4$, $X^6$ and $X^7$ are the same or different and stand for, independently of one another, a hydrogen atom or a halogen atom.

10. A compound according to claim 1, wherein $Y^4$ stands for a $C_1$–$C_5$ alkyl group or a $C_1$–$C_5$ alkyl group or a $C_1$–$C_5$ perfluoroalkyl group.

11. A compound according to claim 1, wherein $Y^5$, $Y^7$ and $Y^8$ are the same or different and stand for, independently of one another, a hydrogen atom or a halogen atom.

12. A compound according to claim 1, wherein:
$R^1$ and $R^2$ are the same or different and stand for a hydrogen atom, a methyl or ethyl group, or $R^1$ and $R^2$ together with the C-atom of the chain stand for a cyclopropyl ring;
$R^3$ stands for a $C_1$–$C_5$ perfluoroalkyl group;
A stands for a benzene, naphthalene or thiophene ring that is optionally substituted by one or more radicals, selected from fluorine atoms, chlorine atoms, bromine atoms, methyl groups, ethyl groups, vinyl groups, hydroxy groups, methoxy groups, ethoxy groups,or $(CH_2)_n$ groups wherein n=3, 4 or 5, which with 2 adjacent C atoms of aromatic compound A forms a ring with n+2 links and which may contain unsaturations;
$X^{3a}$ stands for a hydrogen atom or a $C_1$–$C_5$ alkyl group, or
$X^{3a}$ and $X^{3b}$ are the same or different and stand for a hydrogen atom or a $C_1$–$C_5$ alkyl group;
$X^4$, $X^6$ and $X^7$ are the same or different, and stand for, independently of one another, a hydrogen atom or a halogen atom;
$Y^4$ stands for a $C_1$–$C_5$ alkyl group or a $C_1$–$C_5$ perfluoroalkyl group; and
$Y^5$, $Y^7$ and $Y^8$ are the same or different and stand for, independently of one another, a hydrogen atom or a halogen atom.

13. A compound according to claim 1, in which Ar stands for a ring system of partial formula 5.

14. A compound according to claim 1, in which Ar stands for a ring system of partial formula 8.

15. A compound of claim 1, wherein A stands for a benzene, naphthalene or thiophene ring that is optionally substituted by one or more radicals, selected from fluorine atoms, chlorine atoms, bromine atoms, methyl groups, ethyl groups, $(CH_2)_n$ group (n=3, 4, 5), which with 2 adjacent C atoms of aromatic compound A forms a ring with n+2 members and can contain unsaturations; vinyl groups, hydroxy groups, methoxy groups, ethoxy groups.

16. A compound of formula I according to claim 1, wherein said monocyclic or bicyclic heteroaromatic ring of substituent A is thienyl, furyl, pyranol, pyrrolyl, imidazolyl, pyrazolyl, pyridyl, pyrazinyl, pyrimidinyl, pyridazinyl, thiazolyl, oxazolyl, furazanyl, pyrrolinyl, imidazolinyl, pyrazolinyl, thiazolinyl, triazolyl or tetrazolyl.

17. A compound according to claim 1, wherein said compound is: 1-(4-nitro-3-trifluoromethylanilino)-4-phenyl-2-trifluoromethyl-2-pentanol, or 1-(4-nitro-3-trifluoromethylanilino)-4-phenyl-2-trifluoromethyl-2-pentanol.

18. A pharmaceutical composition comprising at least one compound according to claim 1 and a pharmaceutically compatible carrier.

19. A method for contraception, treating menopausal symptoms or preserving pregnancy, comprising administering to a patient in need of such treatment an effective amount of a compound according to claim 1.

20. A process for the production of a compound according to claim 1

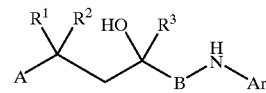

in which A, B, Ar, $R^1$, and $R^2$ have the meaning that is indicated in claim 1, and $R^3$ is $CF_3$ or $C_2F_5$, comprising reacting a carbonyl compound of formula II

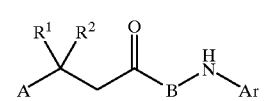

in which A, B, Ar, $R^1$ and $R^2$ have the meaning that is indicated in claim 1 with trifluoromethyl-trimethyl silane or trimethyl-pentafluoroethyl silane, in the presence of a catalyst, to produce a compound of formula I.

21. A process according to claim 20, wherein the catalyst is a fluoride salt or an alkali carbonate.

22. A process for the production of a compound according to claim 1

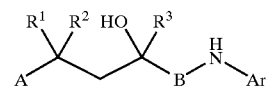

in which
A, B, Ar, $R^1$, $R^2$ and $R^3$ have the meaning that is indicated in claim 1, comprising reacting a compound of formula III

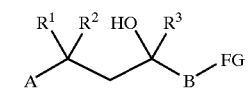

in which A, B, $R^1$, $R^2$ and $R^3$ have the meaning that is indicated claim 1 and FG means a leaving group, with a compound Ar—NH—$R^{11}$, whereby $R^{11}$ means a hydrogen atom or a $C_1$–$C_5$ alkanoyl group, and Ar has the meaning that is indicated in claim 1, and optionally cleaving off radical $R^{11}$.

23. A process according to claim 22, wherein leaving group FG in connection with general formula III is chlorine, bromine, or iodine atoms, a tosylate or mesylate radical or a $C_1$–$C_4$ perfluoroalkylsulfonyloxy radical.

24. A process according to claim 23, wherein the compound of formula III is an acid chloride that is formed as an intermediate product from the corresponding carboxylic acid.

25. A process for the production of a compound according to claim 1

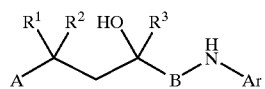 I in which

A, Ar, $R^1$, $R^2$ and $R^3$ have the meaning that is indicated in claim 1, and B means a —$CH_2$ group, comprising reacting a compound of formula IV

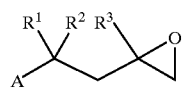 IV in which A, $R^1$, $R^2$ and $R^3$ have the meaning that is indicated in formula I, with a compound of formula Ar—NH—$R^{11}$, whereby $R^{11}$ means a hydrogen atom or a $C_1$–$C_5$ alkanoyl group, and Ar has the meaning that is indicated in claim 1, and optionally then cleaving off radical $R^{11}$.

* * * * *

UNITED STATES PATENT AND TRADEMARK OFFICE
CERTIFICATE OF CORRECTION

PATENT NO.    : 6,548,534 B2
DATED         : April 15, 2003
INVENTOR(S)   : Manfred Lehmann et al.

It is certified that error appears in the above-identified patent and that said Letters Patent is hereby corrected as shown below:

Column 39,
Line 24, reads "$C_1 - C_5,$" should read -- $C_1 - C_5$ --
Line 25, reads "chan" should read -- chain --
Line 30, reads "carbocylic" should read -- carbocyclic --
Line 52, reads "$COOR^{4,}$" should read -- $COOR^4,$ --
Line 56, reads "group:" should read -- group; --
Line 59, reads "$C^1 - C^5$" should read -- $C_1 - C_5$ --

Column 40,
Line 53, reads "comopund" should read -- compound --
Line 56, reads "comound" should read -- compound --
Lines 57 and 59, reads "$R_1$ and $R_2$" should read -- $R^1$ and $R^2$ --

Column 41,
Line 5, reads "$X^{3a,}$" should read -- $X^{3a}$ --
Line 14, reads "for a $C_1$-$C_5$ alkyl group or a $C_1$-$C_5$ alkyl group or a" should read
-- for a $C_1$-$C_5$ alkyl group or a --

Column 42,
Line 59, reads "is chlorine" should read -- is a chlorine --
Line 60, reads "atoms" should read -- atom --

Signed and Sealed this

Thirty-first Day of May, 2005

JON W. DUDAS
*Director of the United States Patent and Trademark Office*